(12) United States Patent
Daley et al.

(10) Patent No.: US 6,348,253 B1
(45) Date of Patent: Feb. 19, 2002

(54) SANITARY PAD FOR VARIABLE FLOW MANAGEMENT

(75) Inventors: Michael Allen Daley, Alpharetta; Jaime Braverman, Atlanta, both of GA (US); Rebecca Lyn Dilnik, Neenah, WI (US); Ronald Lee Edens, Appleton, WI (US); Yvette Lynn Hammonds, Fond du Lac, WI (US); Tamara Lee Mace, Doraville; David Michael Matela, Alpharetta, both of GA (US); Alexander Manfred Schmidt-Foerst, Erlangen (DE); Laura Jane Walker, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/500,503

(22) Filed: Feb. 9, 2000

Related U.S. Application Data

(60) Provisional application No. 60/127,685, filed on Apr. 3, 1999.

(51) Int. Cl.7 ............................. A61F 13/15; B32B 3/24
(52) U.S. Cl. ...................... 428/138; 428/137; 428/131; 428/152; 428/913; 604/385.01; 604/378; 604/358; 604/383
(58) Field of Search ................................ 428/137, 138, 428/131, 152, 913; 604/378, 358, 383, 385.01

(56) References Cited

U.S. PATENT DOCUMENTS

| | | | |
|---|---|---|---|
| 3,029,817 A | 4/1962 | Harwood et al. | 128/290 |
| 3,046,986 A | 7/1962 | Harwood | 128/290 |
| 3,338,992 A | 8/1967 | Kinney | 264/24 |
| 3,341,394 A | 9/1967 | Kinney | 161/72 |
| 3,375,448 A | 3/1968 | Newman et al. | 328/42 |

(List continued on next page.)

FOREIGN PATENT DOCUMENTS

| | | | |
|---|---|---|---|
| CA | 1128704 | 8/1982 | |
| EP | 0 124 365 | 11/1984 | ........... A61F/13/00 |
| FR | 2044554 | 2/1971 | ........... A61F/13/00 |
| GB | 2 111 836 | 7/1983 | ........... A61F/13/16 |
| JP | 8164160 | 6/1996 | |
| WO | 93/09745 | 5/1993 | ........... A61F/13/46 |
| WO | 95/07673 | 3/1995 | ........... A61F/13/15 |
| WO | 95/17870 | 7/1995 | ........... A61F/13/15 |

(List continued on next page.)

OTHER PUBLICATIONS

*Polymer Blends and Composites* by John A. Manson and Leslie H. Sperling, copyright 1976 by Plenum Press, a division of Plenum Publishing Corporation of New York, IBSN 0–306–30831–2, at pp. 273 through 277.

"Quantification of Unidirectional Fiber Bed Permeability" by J. Westhuizen and J. P. Du Plessis in the *Journal of Composite Materials*, 28(7), 1994.

Primary Examiner—William P. Watkins, III
(74) Attorney, Agent, or Firm—James B. Robinson

(57) ABSTRACT

There is provided a feminine hygiene pad comprising a cover adjacent a capillarity fabric having regions of high and low capillarity, which is adjacent a retention layer. In a preferred embodiment, a creped spunbond layer is used as the cover material and a co-apertured intake/distribution layer and transfer delay layer are the capillarity fabric.

Combining these improvements into an integrated absorbent system allows the successful achievement of variable flow management and a successful balance between intake and cover desorption properties. The result is improved multiple intake performance and a clean and dry cover surface during use.

18 Claims, 10 Drawing Sheets

U.S. PATENT DOCUMENTS

| | | | | |
|---|---|---|---|---|
| 3,502,763 | A | 3/1970 | Hartmann | 264/210 |
| 3,542,615 | A | 11/1970 | Dobo et al. | 156/181 |
| 3,667,468 | A | 6/1972 | Nystrand et al. | 128/290 |
| 3,692,618 | A | 9/1972 | Dorschner et al. | 161/72 |
| 3,749,627 | A | 7/1973 | Jones, Sr. | 156/268 |
| 3,802,817 | A | 4/1974 | Matsuki et al. | 425/66 |
| 3,849,241 | A | 11/1974 | Butin et al. | 161/169 |
| 3,855,046 | A | 12/1974 | Hansen et al. | 161/150 |
| 3,860,002 | A | 1/1975 | Kolbach | 128/284 |
| 3,871,378 | A | 3/1975 | Duncan et al. | 128/290 |
| 3,897,784 | A | 8/1975 | Fitzgerald | 128/290 R |
| 3,984,272 | A * | 10/1976 | Teed | 156/201 |
| 4,016,628 | A | 4/1977 | Kolbach | 19/148 |
| 4,027,672 | A | 6/1977 | Karami | 128/284 |
| 4,093,765 | A | 6/1978 | Schmidt | 428/134 |
| 4,100,324 | A | 7/1978 | Anderson et al. | 428/288 |
| RE29,789 | E | 10/1978 | Kolbach | 128/284 |
| 4,340,563 | A | 7/1982 | Appel et al. | 264/518 |
| 4,494,278 | A | 1/1985 | Kroyer et al. | 19/304 |
| 4,636,209 | A | 1/1987 | Lassen | 604/378 |
| 4,640,810 | A | 2/1987 | Laursen et al. | 264/518 |
| 4,795,455 | A | 1/1989 | Luceri et al. | 604/386 |
| 4,818,464 | A | 4/1989 | Lau | 264/510 |
| 4,988,344 | A | 1/1991 | Reising et al. | 604/368 |
| 5,047,023 | A | 9/1991 | Berg | 604/368 |
| 5,057,368 | A | 10/1991 | Largman et al. | 428/397 |
| 5,069,970 | A | 12/1991 | Largman et al. | 428/373 |
| 5,108,820 | A | 4/1992 | Kaneko et al. | 428/198 |
| 5,108,827 | A | 4/1992 | Gessner | 428/219 |
| 5,147,345 | A | 9/1992 | Young et al. | 604/378 |
| 5,231,122 | A | 7/1993 | Palumbo et al. | 524/30 |
| 5,277,976 | A | 1/1994 | Hogle et al. | 428/397 |
| 5,281,208 | A | 1/1994 | Thompson et al. | 604/378 |
| 5,300,054 | A | 4/1994 | Feist et al. | 604/378 |
| 5,304,161 | A | 4/1994 | Noel et al. | 604/378 |
| 5,318,554 | A | 6/1994 | Young et al. | 604/378 |
| 5,330,456 | A | 7/1994 | Robinson | 604/368 |
| 5,336,552 | A | 8/1994 | Strack et al. | 428/224 |
| 5,348,547 | A | 9/1994 | Payne et al. | 604/378 |
| 5,364,382 | A | 11/1994 | Latimer et al. | 604/378 |
| 5,366,451 | A | 11/1994 | Levesque | 604/378 |
| 5,374,260 | A | 12/1994 | Lemay et al. | 604/378 |
| 5,382,400 | A | 1/1995 | Pike et al. | 264/168 |
| 5,397,316 | A | 3/1995 | LaVon et al. | 604/369 |
| 5,429,629 | A | 7/1995 | Latimer et al. | 604/378 |
| 5,437,653 | A | 8/1995 | Gilman et al. | 604/378 |
| 5,439,458 | A | 8/1995 | Noel et al. | 604/378 |
| 5,454,800 | A | 10/1995 | Hirt et al. | 604/378 |
| 5,460,622 | A | 10/1995 | Dragoo et al. | 604/378 |
| 5,466,232 | A | 11/1995 | Cadieux et al. | 604/378 |
| 5,466,410 | A | 11/1995 | Hills | 264/172.11 |
| 5,466,513 | A | 11/1995 | Wanek et al. | 428/218 |
| 5,476,711 | A | 12/1995 | Hebbard et al. | 428/283 |
| 5,486,167 | A | 1/1996 | Dragoo et al. | 604/384 |
| 5,514,104 | A | 5/1996 | Cole et al. | 604/366 |
| 5,527,171 | A | 6/1996 | Soerensen | 425/83.1 |
| 5,549,589 | A | 8/1996 | Horney et al. | 604/366 |
| 5,558,655 | A | 9/1996 | Jezzi et al. | 604/378 |
| 5,562,650 | A | 10/1996 | Everett et al. | 604/378 |
| 5,603,707 | A | 2/1997 | Trombetta et al. | 604/383 |
| 5,607,414 | A | 3/1997 | Richards et al. | 604/378 |
| 5,613,962 | A | 3/1997 | Kenmochi et al. | 604/378 |
| 5,634,915 | A | 6/1997 | Osterdahl | 604/379 |
| 5,647,862 | A | 7/1997 | Osborn, III et al. | 604/378 |
| 5,647,863 | A | 7/1997 | Hammons et al. | 604/378 |
| 5,649,916 | A | 7/1997 | DiPalma et al. | 604/378 |
| 5,662,633 | A | 9/1997 | Doak et al. | 604/378 |
| 5,665,082 | A | 9/1997 | Boulanger | 604/365 |
| 5,669,895 | A | 9/1997 | Murakami et al. | 604/380 |
| 5,695,487 | A | 12/1997 | Cohen et al. | 604/384 |
| 5,728,085 | A | 3/1998 | Widlund et al. | 604/378 |
| 5,730,737 | A | 3/1998 | Widlund et al. | 604/378 |
| 5,785,697 | A | 7/1998 | Trombetta et al. | 604/378 |
| 5,797,894 | A | 8/1998 | Cadieux et al. | 604/378 |
| 5,807,362 | A | 9/1998 | Serbiak et al. | 604/361 |
| 5,817,394 | A | 10/1998 | Alikhan et al. | 428/137 |
| 5,846,232 | A | 12/1998 | Serbiak et al. | 604/385.2 |

FOREIGN PATENT DOCUMENTS

| | | | |
|---|---|---|---|
| WO | 96/33679 | 10/1996 | A61F/13/15 |
| WO | 97/02133 | 1/1997 | B32B/3/28 |
| WO | 97/14384 | 4/1997 | A61F/13/15 |
| WO | 97/18783 | 5/1997 | A61F/13/15 |
| WO | 97/33546 | * 9/1997 | |
| WO | 97/36565 | 10/1997 | A61F/13/46 |
| WO | 97/45083 | 12/1997 | A61F/13/15 |
| WO | 98/13003 | 4/1998 | A61F/13/15 |
| WO | 98/22065 | 5/1998 | A61F/13/15 |
| WO | 98/24960 | 6/1998 | D04H/1/54 |

* cited by examiner

SANITARY PAD FOR VARIABLE FLOW MANAGEMENT

This application claims priority from U.S. Provisional Patent Application No. 60/127,685 filed Apr. 3, 1999.

FIELD OF THE INVENTION

The present invention is an absorbent article for personal care, particularly feminine hygiene products, which can accept liquid, distribute it and retain it.

BACKGROUND OF THE INVENTION

Personal care articles include such items as diapers, training pants, feminine hygiene products such as sanitary napkins, panty-liners and tampons, incontinence garments and devices, bandages and the like. The most basic design of all such articles typically includes a bodyside liner, an outercover (also referred to as a baffle) and an absorbent core disposed between the bodyside liner and the outercover.

Personal care products must accept fluids quickly and hold them to reduce the possibility of leakage outside the product. The product must be flexible and have a pleasing feel on the skin, and even after liquid insult, must not become tight or bind the user. Unfortunately, while previous products have met many of these criteria to varying degrees, a number have not.

In particular, feminine hygiene products for longer term (i.e. overnight) usage are subject to higher and more variable flow rates and fluid loads than are those intended for regular or shorter term usage. Products for overnight usage, therefore, must have the ability to absorb and contain continuous and light flow as well as gushes and sudden heavy flow over the life of the product. It has been found that continuous flow insults in feminine hygiene products average 1 ml/hr, but may be higher, and are not literally continuous or constant, but rather variable in rate and may even pause during a cycle. "Gush flow" is defined as a sudden heavy flow condition and occurs at flow rates of up to 1 ml/sec. During a gush, 1–5 ml of fluid is released from the body onto the product. The term "continuous flow" is used to define any flow which falls outside of the definition of gush flow.

Combining continuous and gush flow conditions results in variable flow. Essentially, "variable flow" is defined as continuous flow with intermittent gush flow occurrences. FIG. 1 is a graph which illustrates the differences between variable flow (diamonds) and continuous flow (squares) over the life of a single product where flow rate volume is on the y-axis in g/hr and time is on the x-axis in hours. This problem of handling gush and continuous flows is termed variable flow management and is defined as the ability to absorb and contain continuous and light flow (1–2 ml/hr) as well as multiple gushes or sudden heavy flow insults (1 ml/sec with a total volume of 1–5 ml) over the life of the product. It is obvious that the challenge of variable flow management is more difficult as the wear time of the product is lengthened, such as in overnight use conditions.

Many feminine care cover materials have low z-directional conductivity, low surface energy, low void volume, and provide little separation between the absorbent core and the user due to their two dimensional structure. Consequently, these covers result in slow and incomplete intake, high rewet, and large surface stains. In addition, typical intake or acquisition layers are low density, high void volume structures which are ideal for fast fluid intake, but because these structures typically have low capillarity, fluid is not adequately desorbed from the cover material, resulting in smearing and surface wetness. Materials which enhance cover desorption are typically high density, high capillarity materials, but because these materials have low void volume and low z-directional permeability, they inherently retard fluid intake.

There remains a need to address variable flow management from the overall product form standpoint, developing a system in which the components are optimized to function together. In such a system, the liner is designed to promote rapid intake and remain clean and dry, there is an intake/distribution material which has the void volume necessary for fast intake and the high capillarity desired for sufficient cover desorption while maintaining an appropriate capillary structure for fluid intake/distribution and the absorbent (retention) layer accepts fluids at the appropriate speed.

An objective of this invention is, therefore, to provide an overall design for a feminine hygiene product, particularly for overnight use, to manage a wide variety of flow conditions including sudden heavy flow insults, or gushes.

SUMMARY OF THE INVENTION

The objects of the invention are achieved by a creped spunbond nonwoven fabric for use as the liner or outer cover, an improved absorbent core using a co-apertured airlaid fabric layer and spunbond nonwoven fabric transfer delay layer, over a fluff retention layer. Combining these improvements into an integrated absorbent system allows the successful achievement of variable flow management and a successful balance between intake and cover desorption properties. The result is improved multiple intake performance and a clean and dry cover surface during use. The material technology developments regarding variable flow management focus on attaining the proper material structure and property balance necessary to achieve fast intake and improve cover desorption, cover staining, and rewet characteristics. These functional properties are provided through improved material technologies and product construction.

BRIEF DESCRIPTION OF THE DRAWINGS

FIG. 3 displays an aperture on the airlaid side of the composite. FIG. 4 displays a close-up of an aperture on the airlaid side of the composite and FIG. 5 displays an aperture from the spunbond (transfer delay) side of the composite.

DEFINITIONS

Figure 1:
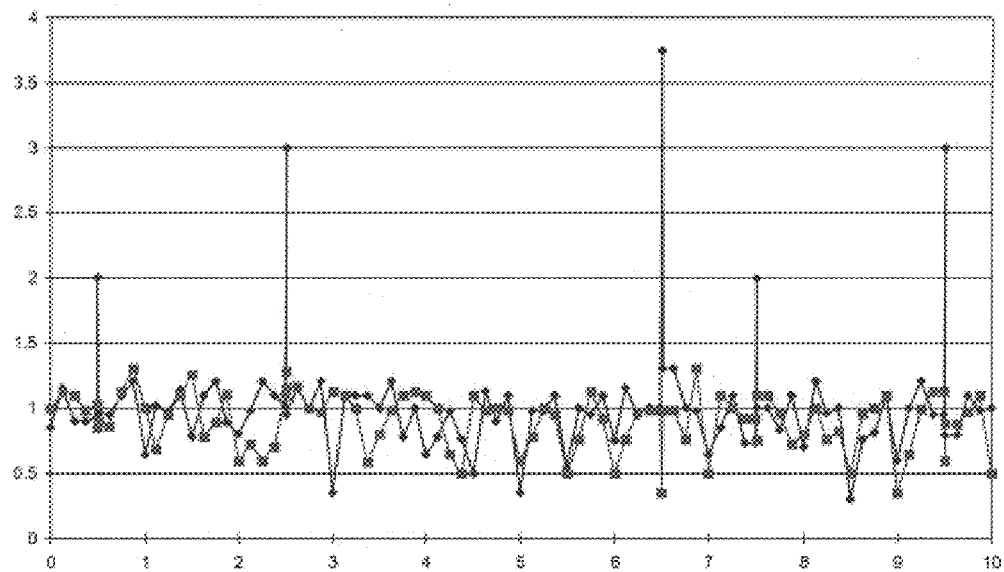
FIG. 1 is a graph of variable flow (diamonds) and continuous flow (squares) over the life of a single product where flow rate volume is on the y-axis in g/hr and time is on the x-axis in hours.

"Disposable" includes being disposed of after use and not intended to be washed and reused.

"Layer" when used in the singular can have the dual meaning of a single element or a plurality of elements.

"Liquid" means a non-particulate substance and/or material that flows and can assume the interior shape of a container into which it is poured or placed.

"Liquid communication" means that liquid is able to travel from one layer to another layer, or one location to another within a layer.

"Longitudinal" means having the longitudinal axis in the plane of the article and is generally parallel to a vertical plane that bisects a standing wearer into left and right body halves when the article is worn. The "transverse" axis lies in the plane of the article generally perpendicular to the longitudinal axis, i.e., so that a vertical plane bisects a standing wearer into front and back body halves when the article is worn.

"Conjugate fibers" refers to fibers that have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. No. 5,277,976 to Hogle et al., and U.S. Pat. Nos. 5,069,970 and 5,057,368 to Largman et al., hereby incorporated by reference in their entirety, which describe fibers with unconventional shapes.

"Biconstituent fibers" refers to fibers that have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

As used herein, the term "machine direction" or MD means the length of a fabric in the direction in which it is produced. The term "cross machine direction" or CD means the width of fabric, i.e. a direction generally perpendicular to the MD.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 35 microns. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers that may be continuous or discontinuous, are generally smaller than 10 microns in average diameter, and are generally tacky when deposited onto a collecting surface.

"Airlaying" is a well-known process by which a fibrous nonwoven layer can be formed. In the airlaying process, bundles of small fibers having typical lengths ranging from about 3 to about 52 millimeters are separated and entrained in an air supply and then deposited onto a forming screen, usually with the assistance of a vacuum supply. The randomly deposited fibers then are bonded to one another using, for example, hot air or a spray adhesive. Examples of airlaying technology can be found in U.S. Pat. Nos. 4,494,278, 5,527,171, 3,375,448 and 4,640,810.

As used herein, the term "coform" means a process in which at least one meltblown diehead is arranged near a chute through which other materials are added to the web while it is forming. Such other materials may be pulp, superabsorbent or other particles, natural polymers (for example, rayon or cotton fibers) and/or synthetic polymers (for example, polypropylene or polyester) fibers, for example, where the fibers may be of staple length. Coform processes are shown in commonly assigned U.S. Pat. No. 4,818,464 to Lau and U.S. Pat. No. 4,100,324 to Anderson et al. Webs produced by the coform process are generally referred to as coform materials.

"Bonded carded web" refers to webs that are made from staple fibers that are sent through a combing or carding unit, which opens and aligns the staple fibers in the machine direction to form a generally machine direction-oriented fibrous nonwoven web. The web is bonded by one or more of several known bonding methods.

Bonding of nonwoven webs may be achieved by a number of methods; powder bonding, wherein a powdered adhesive is distributed through the web and then activated, usually by heating the web and adhesive with hot air; pattern bonding, wherein heated calender rolls or ultrasonic bonding equipment are used to bond the fibers together, usually in a localized bond pattern, though the web can be bonded across its entire surface if so desired; through-air bonding, wherein air which is sufficiently hot to soften at least one component of the web is directed through the web; chemical bonding using, for example, latex adhesives that are deposited onto the web by, for example, spraying; and consolidation by mechanical methods such as needling and hydroentanglement.

An intake/distribution layer is a material which can wick menstrual fluid a distance of 1.2 cm to about 15.25 cm (0.5 to 6 inches) in one hour when one end of the material is placed in an infinite reservoir of menstrual simulant.

"Co-aperture" refers to a material which has been apertured, as well as a process of aperturing, wherein two or more materials are apertured together. The apertures extend from top to bottom of the material and are essentially aligned with each other. Co-aperturing can join the materials either temporarily or permanently through entanglement, physical bonding or chemical bonding. It is preferred that co-aperturing be carried out at ambient temperatures, not at elevated temperatures.

"Personal care product" means diapers, training pants, absorbent underpants, adult incontinence products, swim wear, bandages and other wound dressings, and feminine hygiene products.

"Feminine hygiene products" means sanitary napkins and pads.

"Target area" refers to the area or position on a personal care product where an insult is normally delivered by a wearer.

TEST METHODS

Material Caliper (thickness)

The caliper of a material is a measure of thickness and is measured at 0.05 psi (3.5 g/cm$^2$) with a Starret-type bulk tester, in units of millimeters.

Density

The density of the materials is calculated by dividing the weight per unit area of a sample in grams per square meter (gsm) by the material caliper in millimeters (mm) at 0.05 psi (3.5 g/cm$^2$) and multiplying the result by 0.001 to convert the value to grams per cubic centimeter (g/cc). A total of three samples would be evaluated and averaged for the density values.

Triple Intake Test Procedure

The objective of this test is to determine differences between materials and/or materials, composites or systems of material composites in the rate of intake when 3 fluid insults are applied, with time allowed for fluid to distribute in the material(s) between insults.

Equipment Needed:
  2 acrylic rate blocks.
  P-5000 pipette with RC-5000 tips and foam pipette insert.
  Small beaker
  Menses simulant (made according to directions below), warmed in bath for 30 minutes or more
  Small spatula (stirrer)
  Bench liner
  2 stopwatches
  1–2 timers
  Gauze squares for cleaning simulant
  Procedure: Lay out sample composites according to materials testing plan.
Components are as Follows:
  Top: Cover
  Middle: Capillarity fabric
  Bottom: Retention Layer
Weigh each layer dry, record weight. Put materials back in 3-layer composite. Weigh a dry blotter, record weight and also mark weight on blotter. Place acrylic rate block in middle of sample composite.
Calibrate Pipette:
  Weigh a small empty beaker on the balance.
  Set pipette to 2 mls.
Draw Simulant into Pipette.
  Deliver simulant from pipette into beaker. If balance indicates 2 grams of simulant was delivered, setting is correct. If more or less than 2 grams was delivered, decrease or increase the setting and repeat adjusting pipette and weighing the amount of simulant delivered until 2 grams is delivered.
Simulant Handling:
  Remove simulant from the refrigerator 30 minutes to 1 hour before using and warm in water bath. Before cutting bag nozzle, massage the bag between hands for a few minutes to mix the simulant, which will have separated in the bag. Cut the bag tubing and pour simulant needed into a small beaker. Stir slowly with a small spatula to mix thoroughly. Return bag to the refrigerator if you do not anticipate using all of it. Return bag to water bath if more will be used during the day.
Test:
  Step 1: Center acrylic rate block with funnel on sample. Insult sample composite with 2 mls. simulant, using stopwatch to measure the time from the start of the insult until the fluid is absorbed beneath the cover material. Leave rate block in place for 9 minutes, (use timer). For first sample, after 9 minutes remove the rate block and weigh each layer of the sample. Record the weight. (After 3 minutes timing of the first sample, start testing a second sample going through the same steps.)
  Step 2: For the first sample, repeat Step 1 a second time.
  Step 3: For the first sample, repeat Step 1 a third time.
  Analysis: The fluid loading in each component is calculated as weight after insult subtracted from the weight before insult. The insult time is a direct measurement of time for absorption. Smaller values of intake time refer to a more absorbent sample with larger values of intake time refer to a less absorbent sample.

Capacity

Capacity was measured using the dunk and drip capacity test method. Menses simulant was used as the test fluid. The sample size was modified to a 5.7 cm (2.25") diameter circle. The weight of each sample was recorded. The sample was immersed in a bath of simulant until equilibration, in this case 9 minutes. The sample was removed from the bath and hung vertically at a height of 10.5 cm (12 inches) using a small clip for 10 minutes. The sample was weighed and the weight was recorded. The capacity was determined by subtracting the before weight from the after weight. The capacity in grams/gram was determined by dividing the capacity in grams by the dry weight of the sample.

Horizontal Capillary Wicking Test Procedure

The objective of this test it to determine the horizontal wicking capability of a material as it pulls fluid from a infinite reservoir. Equipment needed: Horizontal wicking stand, menses simulant prepared as described below, ruler, timer.
Procedure:
 Cut materials to 1" (2.54 cm) width and desired length.
 Fill reservoir in horizontal wicking apparatus with menses simulant.
 Place one end of the material in the simulant and lay the rest of the material on the wicking apparatus.
 Start the timer.
 Measure the distance wicked at a given time, or the time to wick to a given distance.

Flat System Testing Procedure

The purpose of this procedure is to determine the fluid handling characteristics of various absorbent systems through analysis of stain length, saturation capacity, and the fluid loading of the system components. The equipment required includes hourglass-shaped acrylic plates (with a 0.25 inch hole in the center) weighing approximately 330 grams, syringes, one-eighth inch I.D. Tygon tubing, pipette pump, menses simulant, and a laboratory balance (accurate to 0.00 g).

Samples to be tested are cut to a desired shape (currently 1.5 inches by 5.5 inches for fluid intake/distribution layers or capillarity fabrics, 1.75 inches by 5.5 inches for transfer delay layers, and 200 mm long hourglass shape for retention layers). The 5.5 inch layers are marked into 1.1 inch sections and the pad layer is marked into sections corresponding to the marks on the 5.5 inch layers when they are centered on the pad layer. Each component is weighed and the weight recorded. The individual components are assembled in to a desired component system maintaining the marked sections aligned and one end is labeled as the top. Syringes are filled with menses simulant and Tygon tubing attached to the syringes. The syringes are raced in a pipette pump which is programmed to deliver a given amount of simulant, currently 30 cc syringes dispensing a specified amount of simulant (usually 10 ml) in one hour. With the open ends of the tubing placed in a beaker, the tubing is primed by running the pump until all air is out of the tubing and simulant is exiting the tubing at the insult end. The component systems to be tested are placed near the pipette pump and a two inch by six inch piece of 25 gsm, 10 d BCW is placed on top of the center of the system over which an acrylic plate is placed, also centered on top of the system. The free end of one tubing is inserted into the hole in the acrylic plate and the pipette pump started to begin the insults. At the end of the insult period, the tubing and acrylic plates are removed. The BCW is then carefully removed without moving the underlying layers and discarded. Each layer is then individually weighed and the weight recorded. Then, beginning at the end labeled as the top, each marked section is cut and weighed. The stain length for each layer is measured and recorded and the data entered into a spreadsheet for graphing and analysis. The fluid loading (g/g) is calculated by dividing the amount of fluid absorbed in a material by the dry weight of the material. The fluid saturation is calculated by dividing the fluid loading by the stain length.

Demand Absorbency Wicking Capability

The objective of this test is to determine the fluid handling characteristics of various absorbent systems through analysis of stain length, saturation capacity, and fluid loadings of the system components.

Equipment needed: Hourglass-shaped acrylic plates (with 0.25" (6.35 mm) hole in the center) weighing approximately 330 grams; syringes; ⅛ inch (3.175 mm) internal diameter (ID) tubing (e.g. Tygon®); pipette pump; menses simulant prepared as described below; laboratory balance (accurate to 0.00 g).
Procedure:
 1. Cut components to desired shape; 1.5 inches (3.8 cm) by 6.0 inches (15.2 cm) for intake/distribution layers, 3.0 inches (7.6 cm) by 6.0 inches for spunbond nonwoven fabric transfer delay and perimeter layers.
 2. Mark 6.0 inch layers into 1.2 inch (3 cm) sections. If the perimeter layer is oval, mark into sections corresponding to the marks on the intake/distribution strip when centered on the perimeter layer.
 3. Weigh each component and record the weight.
 4. Assemble the individual components into the desired absorbent system keeping the marked sections aligned. Label one end as the top.
 5. Fill the syringes with menses simulant and attach tubing to syringes.
 6. Place the syringes in the syringe pump.
 7. Program the size of the syringe into the syringe pump.
 8. Program the pump (currently using 30 cc syringes dispensing at a rate of 10 ml. per hour.
 9. With the open ends of the tubing placed in a beaker, prime tubing by running pump until all air is out of tubing and simulant is exiting the tubing at the open end.
 10. Place the component systems to be tested near the syringe pump, place a 2 inch (5.1 cm) by 6 inch (approximately) piece of 25 gsm, 10 denier bonded carded web material on the top layer of the absorbent system to prevent wicking on the acrylic plate, and place an acrylic plate centered on the top of the system.
 11. Insert the open end of one tubing into the hole in the acrylic plate. Repeat for the remaining systems to be tested.
Testing:
 1. Start the pipette pump to begin the insult.
 2. Ad 3 mls. of menses simulant at a rate of 10 mls per hour.

3. After 3 mls have been insulted into the product, add weights to the acrylic plate to achieve a pressure of 0.08 psi.
4. Continue the insults for another 5 mls, so that a TOTAL of 8 mls is insulted.
5. At the end of the insult period, remove the tubing and acrylic plates. Carefully remove the bonded carded web without moving the underlying layers and discard it.
6. Take photos of the component system and layers and print them.
7. Weigh each layer individually and record the weight.
8. Beginning at the end labeled as the top, cut and weigh the first marked sections and the weight. Repeat for remaining sections and layers.
9. Measure and record the stain length for each layer.
10. Enter the data in a spreadsheet for graphing and analysis.

Preparation of Menses Simulant

In order to prepare the fluid, blood, in this case defibrinated swine blood, was separated by centrifugation at 3000 rpm for 30 minutes, though other methods or speeds and times may be used if effective. The plasma was separated and stored separately, the buffy coat removed and discarded and the packed red blood cells stored separately as well.

Eggs, in this case jumbo chicken eggs, were separated, the yolk and chalazae discarded and the egg white retained. The egg white was separated into thick and thin portions by straining the white through a 1000 micron nylon mesh for about 3 minutes, and the thinner portion discarded. Note that alternative mesh sizes may be used and the time or method may be varied provided the viscosity is at least that required. The thick portion of egg white which was retained on the mesh was collected and drawn into a 60 cc syringe which was then placed on a programmable syringe pump and homogenized by expelling and refilling the contents five times. In this example, the amount of homogenization was controlled by the syringe pump rate of about 100 ml/min, and the tubing inside diameter of about 0.12 inches. After homogenizing the thick egg white had a viscosity of about 20 centipoise at 150 sec$^{-1}$ and it was then placed in the centrifuge and spun to remove debris and air bubbles at about 3000 rpm for about 10 minutes, though any effective method to remove debris and bubbles may be used.

After centrifuging, the thick, homogenized egg white, which contains ovamucin, was added to a 300 cc Fenwal® Transfer pack using a syringe. Then 60 cc of the swine plasma was added to the transfer pack. The transfer pack was clamped, all air bubbles removed, and placed in a Stomacher lab blender where it was blended at normal (or medium) speed for about 2 minutes. The transfer pack was then removed from the blender, 60 cc of swine red blood cells were added, and the contents mixed by hand kneading for about 2 minutes or until the contents appeared homogenous. A hematocrit of the final mixture showed a red blood cell content of about 30 weight percent and generally should be at least within a range of 28–32 weight percent for artificial menses made according to this example. The amount of egg white was about 40 weight percent.

The ingredients and equipment used in the preparation of this artificial menses are readily available. Below is a listing of sources for the items used in the example, though of course other sources may be used providing they are approximately equivalent.

Blood (swine): Cocalico Biologicals, Inc., 449 Stevens Rd., Reamstown, Pa. 17567, (717) 336-1990.

Fenwal® Transfer pack container, 300 ml, with coupler, sample 4R2014: Baxter Healthcare Corporation, Fenwal Division, Deerfield, Ill. 60015.

Harvard Apparatus Programmable Syringe Pump model no. 55-4143: Harvard Apparatus, South Natick, Mass. 01760.

Stomacher 400 laboratory blender model no. BA 7021, serial no. 31968: Seward Medical, London, England, UK.

1000 micron mesh, item no. CMN-1000-B: Small Parts, Inc., PO Box 4650, Miami Lakes, Fla. 33014-0650, 1-800-220-4242.

Hemata Stat-II device to measure hemocrits, serial no. 1194Z03127: Separation Technology, Inc., 1096 Rainer Drive, Altamont Springs, Fla. 32714.

Rate Block Intake Test

This test is used to determine the intake time of a known quantity of fluid into a material and/or material system. The test apparatus consists of a rate block 10 as shown in FIG. 1. A 4"×4" piece of absorbent 14 and cover 13 are die cut. The specific covers are described in the specific examples. The absorbent used for these studies was standard and consisted of 250 g/m$^2$ airlaid made of 90% Coosa 0054 and 10% HC T-255 binder. The total density for this system was 0.10 g/cc. The cover 13 was placed over the absorbent 14 and the rate block 10 was placed on top of the two materials. 2 mL of a menses simulant was delivered into the test apparatus funnel 11 and a timer started. The fluid moved from the funnel 11 into a channel 12 where it was delivered to the material or material system. The timer was stopped when all the fluid was absorbed into the material or material system as observed from the chamber in the test apparatus. The intake time for a known quantity of known fluid was recorded for a given material or material system. This value is a measure of a material or material systems absorbency. Typically, five to ten repetitions were performed, and average intake time was determined.

Rewet Test

This test is used to determine the amount of fluid that will come back to the surface when a load is applied. The amount of fluid that comes back through the surface is called the "rewet" value. The more fluid that comes to the surface, the larger the "rewet" value. Lower rewet values are associated with a dryer material and, thus, a dryer product. In considering rewet, three properties are important: (1) intake, if the material/system does not have good intake then fluid can rewet, (2) ability of absorbent to hold fluid (the more the absorbent holds on to the fluid, the less is available for rewet), and (3) flowback, the more the cover prohibits fluid from coming back through the cover, the lower the rewet. In our case, we evaluated cover systems where the absorbent was maintained constant and, thus, we were only concerned with properties (1) and (3), intake and flowback, respectively.

A 4"×4" piece of absorbent and cover was die cut. The absorbent used for these studies was standard and consisted of a 250 g/m$^2$ airlaid made of 90% Coosa 0054 and 10% HC T-255 binder. The total density for this system was 0.10 g/cc. The cover was placed over the absorbent and the rate block was placed on top of the two materials. In this test, 2 mL of menses simulant are insulted into the rate block apparatus and are allowed to absorb into a 4"×4" sample of the cover material which is placed on top of a 4"×4" absorbent piece. The fluid is allowed to interact with the system for one minute and the rate block rests on top of the materials. The material system cover and absorbent are placed onto a bag filled with fluid. A piece of blotter paper is weighed and placed on top of the material system. The bag is traversed vertically until it comes into contact with an acrylic plate above it, thus pressing the whole material system against the plate blotter paper side first. The system is pressed against the acrylic plate until a total pressure of 1 psi is applied. The pressure is held fixed for three minutes, after which the pressure is removed and the blotter paper is weighed. The blotter paper retains any fluid that was transferred to it from the cover/absorbent system. The difference in weight between the original blotter and the blotter after the experiment is known as the "rewet" value. Typically, five to ten repetitions of this test were performed, and average rewet was determined.

Intake/Staining Test

An intake/staining test was developed which enables the stain size, intensity, and fluid retention in components to be observed with fluid flow rate and pressure. Menses simulant was used as the test fluid. A 4"×4" piece of absorbent and cover were die cut. The absorbent used for these tests was standard and consisted of a 250 g/m² airlaid made of 90% of Coosa 0054 and 10% HC T-255 binder. The total density for this system was 0.10 g/cc. A material system, cover and core measuring 4"×4", was placed underneath an acrylic plate with an ⅛ inch diameter hole bored into the center. A piece of ⅛ inch tubing was connected to the hole with a fitting. Menses simulant was delivered to the sample using a syringe pump at a specified rate and for a specified volume. The pump was programmed to deliver a total volume of 1 mL to the samples, where the samples were under pressures of 0 psi, 0.0078 psi, and 0.078 psi. These pressures were applied using a weight which was placed on top of the acrylic plates and distributed evenly. The flow rate of the pump was programmed to deliver fluid at a rate of 1 mL/sec. The stain size for the cover materials was measured manually, and the amount of fluid in each component of the system was measured by weight before and after absorption of the fluid. The stain intensity was evaluated qualitatively by comparison of samples. Staining information was recorded using a digital camera and could be further analyzed with image analysis.

Permeability

Permeability is obtained from a measurement of the resistance by the material to the flow of liquid. A liquid of known viscosity is forced through the material of a given thickness at a constant flow rate and the resistance to flow, measured as a pressure drop is monitored. Darcy's Law is used to determine permeability as follows:

$$\text{Permeability} = [\text{flow rate} \times \text{thickness} \times \text{viscosity} / \text{pressure drop}] \quad \text{Equation (1)}$$

where the units are:

permeability: $cm^2$ or darcy 1 darcy=$9.87 \times 10^{-9}$ $cm^2$ flow rate: cm/sec viscosity: pascal-sec pressure drop: pascals The apparatus consists of an arrangement wherein a piston within a cylinder pushes liquid through the sample to be measured. The sample is clamped between two aluminum cylinders with the cylinders oriented vertically. Both cylinders have an outside diameter of 3.5", an inside diameter of 2.5" and a length of about 6". The 3" diameter web sample is held in place by its outer edges and hence is completely contained within the apparatus. The bottom cylinder has a piston that is capable of moving vertically within the cylinder at a constant velocity and is connected to a pressure transducer that capable of monitoring the pressure of encountered by a column of liquid supported by the piston. The transducer is positioned to travel with the piston such that there is no additional pressure measured until the liquid column contacts the sample and is pushed through it. At this point, the additional pressure measured is due to the resistance of the material to liquid flow through it.

The piston is moved by a slide assembly that is driven by a stepper motor. The test starts by moving the piston at a constant velocity until the liquid is pushed through the sample. The piston is then halted and the baseline pressure is noted. This corrects for sample buoyancy effects. The movement is then resumed for a time adequate to measure the new pressure. The difference between the two pressures is the pressure due to the resistance of the material to liquid flow and is the pressure drop used in Equation (1). The velocity of the piston is the flow rate. Any liquid whose viscosity is known can be used, although a liquid that wets the material is preferred since this ensures that saturated flow is achieved. The measurements disclosed herein were carried out using a piston velocity of 20 cm/min, mineral oil (Peneteck Technical Mineral Oil manufactured by Penreco of Los Angeles, Calif.) of a viscosity of 6 centipoise.

Alternatively, permeability can be calculated from the following equation:

$$\text{Permeability} = 0.051 * R * (1-\text{Porosity}) * (\text{Porosity}/(1-\text{Porosity}))^{2.75} \quad \text{Equation (2)}$$

where R=fiber radius and $$\text{Porosity} = 1 - (\text{web density/fiber density}) \quad \text{Equation (3)}$$

Reference for Equation (2) can be found in the article "Quantification of Unidirectional Fiber Bed Permeability" by J. Westhuizen and J. P. Du Plessis in the *Journal of Composite Materials*, 28(7), 1994. Note that the equations show that permeability can be determined if fiber radius, web density and fiber density are known.

Conductance is calculated as permeability per unit thickness and gives measure of the openness of a particular structure and, thus, an indication of the relative ease at which a material will pass liquid. The units are darcies/mil.

DETAILED DESCRIPTION OF THE INVENTION

In its broadest embodiment, the invention is feminine hygiene pad comprising a rapid intake cover adjacent a capillarity fabric having regions of varying capillarity which allows the passage of fluids in particular areas, and which is adjacent an absorbent core retention layer. The fabrics used in the practice of this invention may be made by a variety of processes including airlaying, spunbonding, meltblowing, carding, coform and foaming processes, though airlaying for the intake/distribution layer and spunbonding for the transfer delay layer are preferred. The various layers may be made from synthetic polymer and natural fibers. Particularly preferred because of cost are polyolefins like polyethylene and polypropylene.

It is important that the cover rapidly draw insults into the product. A number of materials provide such intake properties. These include pin apertured films, vacuum apertured films, apertured nonwovens and co-apertured film/ nonwoven laminates, conjugate fiber spunbond fabrics, creped spunbond fabrics, airlaid fabrics, bonded carded webs, spunlace fabrics, etc. A number of fabric types which may be unsuitable initially may be made acceptable through the use of topical chemical treatments and mechanical processing. Any material which, when combined with an absorbent core, permits rapid intake, low staining, low rewet and low fluid retention under all flow conditions would be suitable.

The capillarity fabric is an intake/distribution layer which may be made from a variety of fibers and mixtures of fibers including synthetic fibers, natural fibers including, mechanically and chemically softened pulp, staple fibers, slivers, meltblown and spunbond fibers, superabsorbents and the like. The fibers in such a web may be made from the same or varying diameter fibers and may be of different shapes such as pentalobal, trilobal, elliptical, round, etc. The intake/distribution layer may be made by a number of methods, including airlaying, hydroentangling, bonding and carding, and coforming, though airlaying is preferred.

The transfer delay layer may also be made from a variety of fibers in a variety of shapes and sizes. The transfer delay layer may be made according to a number of processes such as spunbonding, carding, meltblowing and film forming, though spunbonding is preferred.

The retention layer materials may be made from materials or substances known in the art to absorb liquid as well as any others that may be developed for that purpose. Examples include fast and slow superabsorbents, pulps, and mixtures thereof. Mixtures of superabsorbents and pulp used as retention materials may be used in ratios of between about 100/0 and 0/100 by weight, more particularly between about 80/20 and 20/80.

Synthetic fibers include those made from polyamides, polyesters, rayon, polyolefins, acrylics, superabsorbents, Lyocel regenerated cellulose and any other suitable synthetic fibers known to those skilled in the art. Synthetic fibers may also include kosmotropes for product degradation.

Many polyolefins are available for fiber production, for example polyethylenes such as Dow Chemical's ASPUN® 6811A linear low density polyethylene, 2553 LLDPE and 25355 and 12350 high density polyethylene are such suitable polymers. The polyethylenes have melt flow rates, respectively, of about 26, 40, 25 and 12. Fiber forming polypropylenes include Exxon Chemical Company's Escorene® PD 3445 polypropylene and Montell Chemical Co.'s PF-304. Many other polyolefins are commercially available.

Natural fibers include wool, cotton, flax, hemp and wood pulp. Pulps include standard soft-wood fluffing grade such as CR-1654 from Coosa Mills of Coosa, Ala., high bulk additive formaldehyde free pulp (HBAFF) available from the Weyerhaeuser Corporation of Tacoma, Wash., and is a which is a crosslinked southern softwood pulp fiber with enhanced wet modulus, and a chemically cross-linked pulp fiber such as Weyerhaeuser NHB-416. HBAFF has a chemical treatment that sets in a curl and twist, in addition to imparting added dry and wet stiffness and resilience to the fiber. Another suitable pulp is Buckeye HP2 pulp and still another is IP Supersoft from International Paper Corporation. Suitable rayon fibers are 1.5 denier Merge 18453 fibers from Courtaulds Fibers Incorporated of Axis, Ala.

Various superabsorbents in a number of forms are available. Commercially available examples include FAVOR® 870 superabsorbent spheres from the Stockhausen Company of Greensboro, N.C. 27406 which is a highly crosslinked surface superabsorbent, XL AFA 94-21-5 and XL AFA-126-15, which are 850 to 1400 micron suspensions of polymerized polyacrylate particles from The Dow Chemical Company of Midland, Mich., and SANWET® IM 1500 superabsorbent granules supplied by KoSA Inc. (formerly Trevira Inc. and formerly Hoechst-Celanese), PO Box 4, Salisbury, N.C. 28145-0004.

Binders may also be included in the spunbond or airlaid layers in order to provide mechanical integrity to the web. Binders include fiber, liquid or other binder means which may be thermally activated. Preferred fibers for inclusion are those having a relatively low melting point such as polyolefin fibers. Lower melting polymers provide the ability to bond the fabric together at fiber cross over points upon the application of heat. In addition, fibers having as at least one component a lower melting polymer, like conjugate and biconstituent fibers, are suitable for the practice of this invention. Fibers having a lower melting polymer are generally referred to as "fusible fibers." By "lower melting polymers" what is meant are those having a glass transition temperature less than about 175° C. Exemplary binder fibers include conjugate fibers of polyolefins and/or polyamides, and liquid adhesives. Two such suitable binders are sheath core conjugate fibers available from KoSA Inc. under the designation T-255 and T-256, though many suitable binder fibers are known to those skilled in the art, and are made by many manufacturers such as Chisso and Fibervisions LLC of Wilmington, Del. A suitable liquid binder is Kymene® 557LX binder available from Fibervisions LLC.

Once produced, the web must be adequately stabilized and consolidated in order to retain its shape. The inclusion of a sufficient amount of fusible fibers and subsequent thermal bonding is the preferred method for obtaining adequate stabilization. It's believed that this method allows adequate bonding in the center of a thick material as well as on the surface.

Figure 10:
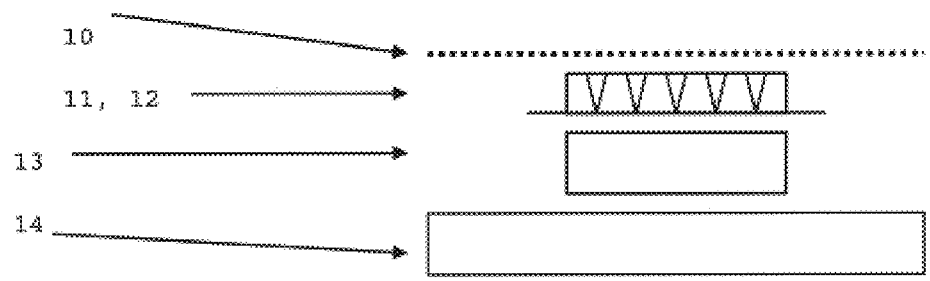
FIG. 10 depicts one example of a product form for a feminine hygiene product for overnight use.

One example of a product form for a feminine hygiene product for overnight use, as depicted in FIG. 10; it has an absorbent system composed of a creped spunbond fabric cover 10, a co-apertured airlaid intake/distribution layer 11 and a spunbond fabric transfer delay layer 12, a fluff retention layer 13, and a shaped fluff perimeter layer 14.

A specific example would be a 13.6 gsm (0.4 osy) spunbond cover, creped 30 percent to a basis weight of 20.3 gsm (0.6 osy) and treated with 0.3 weight percent AHCOVEL® Base N-62 surfactant and a capillarity fabric made of a co-apertured 175 gsm, 90 weight percent Weyerhaeuser NF405 and 10 weight percent KoSa T-255 fiber airlaid fabric at 0.12 g/cc and a 27 gsm (0.8 osy) spunbond transfer delay layer made of polypropylene. A retention layer made of 500 gsm fluff, 0.06–0.09 g/cc, of Weyerhaeuser NF-405 is included. A second retention layer made of 600 gsm fluff, 0.06–0.09 g/cc, of Weyerhaeuser NF-405 is also included.

Under continuous flow conditions, fluid is rapidly absorbed into the airlaid intake/distribution layer through the wettable and highly permeable creped spunbond cover. The spunbond fabric transfer delay layer, which is co-apertured to the airlaid intake/distribution layer, prevents premature fluid transfer to the underlying retention layer and forces fluid to distribute lengthwise in the product.

Its believed by the inventors that Initial insults are absorbed by and remain in the airlaid intake/distribution layer until 30–40% saturation levels are achieved (approximately 3–4 grams of fluid). At this point of saturation in the airlaid intake/distribution layer, fluid begins to transfer from the intake/distribution layer, through the transfer delay layer to the underlying fluff retention layer. The fluff retention layer, centered below the transfer delay layer, absorbs fluid that passes through the transfer delay layer as the product is insulted. The transfer delay layer controls the amount of fluid that is passed to the absorbent below and facilitates intake/distribution. As the amount of fluid in the airlaid intake/distribution layer increases, the amount of fluid transferred through the transfer delay layer to the underlying fluff increases. By transferring fluid based on the fluid saturation level, the transfer delay prevents high fluid saturation levels (>80%) from occurring in the airlaid intake/distribution layer. This function allows the airlaid intake/distribution layer to maintain void volume for additional insults. The airlaid intake/distribution layer returns toward an equilibrium level of 30–40% fluid saturation during use between insults.

While the shape of the various layers is not considered critical to the success of the invention, it should be noted that the airlaid intake/distribution and fluff retention layers may also incorporate a reduced dimension rectangular strip geometry which prevents fluid from wicking to the pad edges. The combination of intake/distribution and transfer delay technology, aided to some degree by the specific material geometry, forces the fluid to remain in the center of the product in the x, y, and z directions. The asymmetrical (e.g. hourglass shaped) perimeter layer is also available to hold fluid under medium to high product fluid loads (greater than 5 g), but primarily serves as a product shaping component. It should be noted that the retention layer shape may be the same as or different from that of the perimeter layer and that either may have a rectangular, hourglass, racetrack or other shape. In addition, embossing may be added to the retention and/or perimeter layer to enhance the integrity of the layer.

Figure 11:
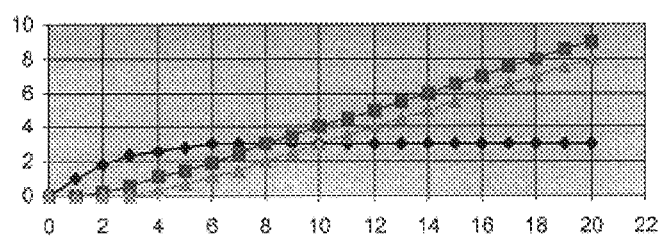
FIG. 11 illustrates the theoretical fluid loading profile for the feminine hygiene product of FIG. 10.

The theoretical fluid loading profile for this feminine hygiene product is illustrated in FIG. 11. FIG. 11 is a graph of the component liquid content (or loading) in grams on the Y-axis and total product loading in grams on the X-axis. The airlaid intake/distribution is depicted by diamonds on the graph, the retention layer by squares, and the perimeter layer as triangles. At low loadings (0–3 ml), the fluid is mainly absorbed into the airlaid intake/distribution layer. As fluid loading increases (3–5 ml), the fluid begins to transfer through the transfer delay layer into the retention layer and slightly into the perimeter layer. At this time, very little fluid from additional insults is held in the airlaid intake/distribution layer. The airlaid intake/distribution layer continually regenerates its void volume by transferring fluid to the retention layer so subsequent insults can be accommodated. At higher loadings (>5 ml), the retention layer holds the majority of the fluid due to its high void volume. The perimeter layer has the capacity to retain any residual fluid which is passed through the retention layer because of localized saturation. The perimeter layer also provides further coverage for insults outside of the target area.

Under gush situations (>1 ml/sec and 1–5 ml/insult), the feminine hygiene product performs similarly to the theoretical filling profile described above but also demonstrates several additional functional characteristics. When a gush occurs, it is absorbed into the void volume of the highly permeable creped cover and into the airlaid intake/distribution layer. Under gush situations, the apertures in the airlaid intake/distribution layer provide internal void volume and increased permeability which assist intake and storage of fluid. The apertures assist in storage of fluid by providing an immediate internal reservoir for fluid until it is absorbed into the surrounding airlaid structure. This functionality is critical since a gush insult happens so fast that momentary localized saturation occurs in the un-apertured portions of the airlaid fabric. During gush insults, the apertures also provide a direct pathway to the underlying fluff retention layer so that fluid can be immediately transferred to the fluff layer and void volume can be quickly regenerated in the airlaid layer. By regenerating void volume, the airlaid layer is available for future insults.

Immediately after the gush is absorbed, the intake/distribution and transfer characteristics of the co-apertured intake/distribution/transfer delay system take over. The fluid distributes in the airlaid intake/distribution layer and transfers through the transfer delay layer until the equilibrium level of 30–40% fluid saturation is achieved in the airlaid intake/distribution layer. This equilibration process again helps in regenerating the void volume in the intake/distribution layer so that it is available to take additional insults. A suitable intake/distribution layer horizontally wicks menses a distance of from about 1.2 cm to about 15.25 cm.

Cover Material Properties

It is important that the cover rapidly draw insults into the product. A number of materials provide such intake properties. These include pin apertured films, vacuum apertured films, apertured nonwovens and co-apertured film/nonwoven laminates, conjugate fiber spunbond fabrics, creped spunbond fabrics, airlaid fabrics, bonded carded webs, spunlace fabrics, etc. A number of fabric types which may be unsuitable initially may be made acceptable through the use of topical chemical treatments and mechanical processing. Any material which, when combined with an absorbent core, permits rapid intake, low staining, low rewet and low fluid retention under all flow conditions would be suitable.

Figure 8:
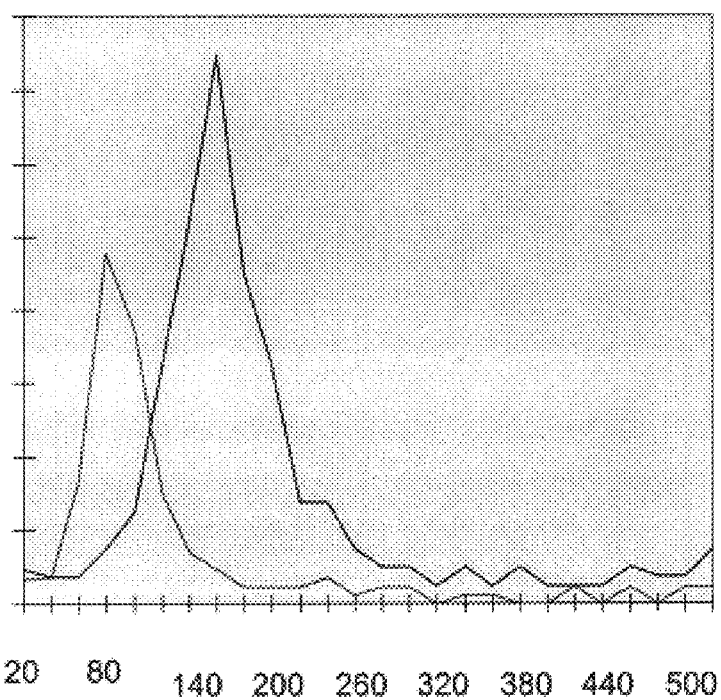
FIG. 8 is a graph of the pore size distribution for creped and uncreped spunbond cover materials.

Creped spunbond nonwoven fabric is preferred as the feminine care product cover material since it creates benefits that can be leveraged in the design of a gush management absorbent core. These benefits are a result of the fundamental property changes that occur during the creping process. In order to characterize the structural differences that exist between standard spunbond fabric and creped spunbond fabric and identify the impact of creping the spunbond fabric on gush management, two samples are compared. One sample was a 3.5 dpf, 20.3 gsm (0.6 osy) polypropylene spunbond and the other was a 3.5 dpf, 13.6 gsm (0.4 osy) polypropylene spunbond creped 30% to an effective 20.3 gsm basis weight. Both materials were treated with 0.30 weight percent AHCOVEL surfactant. Structural differences can be best characterized by comparing the pore size distributions of the base material to the creped material. FIG. 8 is a graph of the pore size distribution for these two samples. In FIG. 8, the Y-axis is the pore volume in cc/g and the X-axis is pore radius in microns. The creped spunbond fabric is denoted by the line which peaks first on the left.

The peak pore size for the standard spunbond fabric is 80 microns while the creped spunbond fabric peak pore size is 170 microns. The peak pore size increases with creping because, its believed, primary bonds are deformed and z-directional pores are formed, thereby creating a three dimensional pore structure. The overall increase in caliper results in an increase in total pore volume and a corresponding shift to a larger pore size. For comparison, the pore structure of standard spunbond fabric is two dimensional due to its relatively flat surface structure. The increased permeability and larger pore size of the creped spunbond fabric allows fluid to enter the product more easily. In addition, the large pores are better suited for handling the variety of menstrual fluid types that are associated with heavy and/or gush flow.

Figure 9:
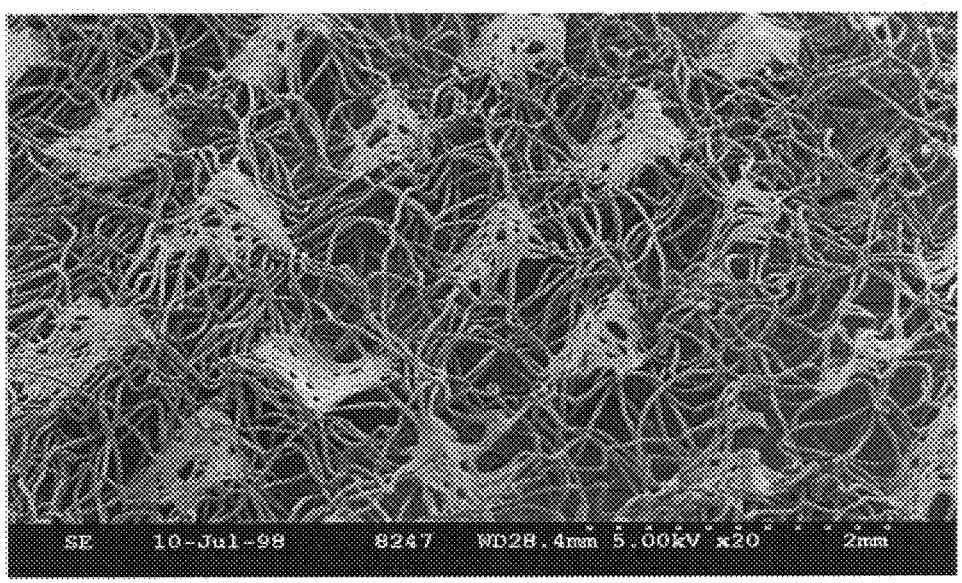
FIG. 9 shows the three dimensional structure of the creped spunbond fabric cover in an SEM image.

The breadth of the pore size distribution also increases with creping. The area under each of the curves in FIG. 8 represents a measure of the pore volume for the material. As illustrated by the curves, the pore volume is much higher for the creped spunbond fabric compared to the standard spunbond fabric. The increase in total pore volume facilitates fluid intake and allows the product to accommodate a variety of flow types without failure. FIG. 9 shows the three dimensional structure of the creped spunbond fabric cover in an SEM image at a magnification of one inch equals 2 mm.

Additional structural differences between standard and creped spunbond fabrics are outlined in Table 1. As can be seen from Table 1, the thickness of the creped spunbond fabric is about 2.5 times that of the uncreped spunbond fabric. The thickness creates a barrier between the product and the woman's body and promotes skin dryness by reducing wetness typically caused by rewet. Second, the permeability of the creped spunbond fabric is significantly higher than that of the standard spunbond fabric. This increase in permeability is believed to be due to two factors: the decrease in spunbond fabric density produced by creping and the partial orientation of fibers out of the plane of the fabric. Both of these factors decrease the amount of fiber surface that is in contact with the testing media and thus provide lower resistance to flow, again facilitating fast intake.

TABLE 1

Comparison of Structural Properties for Spunbond fabric and Creped Spunbond fabric

| | Spunbond (20.3 gsm, 3.5 dpf) | Creped Spunbond (20.3 gsm, 3.5 dpf) |
| --- | --- | --- |
| Thickness (mm) | 0.254 | 0.66 |
| Permeability (Darcies) | 511 | 3953 |

The differences in structural properties of the fabrics have a profound effect on the functional properties that these fabric exhibit, as described above. Table 2 displays how several functional properties improve dramatically for the creped spunbond cover fabric compared to standard uncreped spunbond fabric. Results are indicative of the contributions of the creped cover alone when tested over a standard airlaid absorbent core.

TABLE 2

Comparison of Functional Properties for Spunbond and Creped Spunbond fabric

| | Average Intake Time (seconds) | Average Rewet (grams) | Average Stain Size (mm²) | Average Fluid Retention (grams) |
| --- | --- | --- | --- | --- |
| Spunbond (20.3 gsm, 3.5 dpf | 32 | 0.45 | 751 | 0.043 |
| Creped Spunbond (20.3 gsm, 3.5 dpf) | 17 | 0.07 | 619 | 0.015 |

The intake time is cut in half due to the increase in permeability and void volume that is introduced by creping. The creped spunbond fabric cover results in rewet that is 16% of the rewet that occurs with the standard spunbond fabric cover. This reduction occurs due to the increase in permeability, pore size, and thickness of the creped spunbond fabric cover. The increase in permeability promotes fluid transport to the absorbent core and the large average pore size ensures that fluid is not held tightly within the inter-fiber spacing of the cover, thus being easily desorbed by the absorbent core. This reduces fluid retention in the cover which reduces rewet and staining by reducing the amount of fluid that is in contact with or in close proximity to the top surface of the cover. The increased loft of the structure provides separation from the absorbent core and thus provides a barrier to fluid flowback. Some reduction in stain intensity also occurs due to masking which occurs as a result of the material thickness.

The functional improvements of faster intake and reduced rewet, retention, and stain size make the creped spunbond cover an ideal candidate for incorporation into a gush management absorbent system. The creped spunbond cover should be light weight, preferably between about 10 and 30 gsm, more particularly between about 15 and 25 gsm, with between about 20 and 50 percent creping, more particularly between about 25 and 40 percent.

Co-apertured Intake/Distribution Layer/Transfer Delay

The intake/distribution layer and the transfer delay layer are co-apertured using mechanical pin aperturing, though holes may also be provided by die cutting or forming the materials in such a way that they are produced with holes in place. The objective is the production of a material which has regions of high and low capillarity so as to produce a "capillarity fabric" which preferentially allows the movement of fluid in some areas but restricts of prohibits it in others. The fluid transfer delay layer for personal care absorbent products in accordance with this invention is designed to enhance distribution in the x-y plane by delaying the transfer of fluid from the intake/distribution layer to the retention layer. The preferred form of capillarity fabric is produced by the co-aperturing of an airlaid fabric and spunbond fabric, though an apertured nonwoven fabric or an embossed nonwoven fabric may also function well. The co-aperturing of the intake/distribution and transfer delay layers provides unique characteristics for the management of gush insults. A unique material is created with a tri-modal pore structure consisting of 1) pores in the bulk of the airlaid which are characteristic of the original structure in the case of airlaid materials, 2) large void spaces defined by the pins of the aperturing process, and 3) small interfacial pores surrounding the perimeter of the apertures. The apertures are typically characterized by an open structure which tapers into a rounded cone-like structure as observed from the airlaid side of the composite. The interfacial pores are smaller than the surrounding pores due to densification and fiber relocation which results from the aperturing process.

The transfer delay layer provides a permeability and wettability gradient between the intake/distribution layer and the underlying retention layer by preventing intimate contact between the two layers. The transfer delay layer should have relatively low permeability and wettability so it will promote lateral fluid distribution in the intake/distribution layer under continuous flow conditions and so control fluid movement in the Z-direction. The wettability of the transfer delay layer may be modified by topical chemical treatments known to those skilled in the art to affect the hydrophobicity of a material. Some suitable chemicals for modification of wettability are marketed under the tradenames AHCOVEL®, Glucopon®, Pluronics®, Triton®, and Masil SF-19®. The transfer delay promotes lateral (X-Y) distribution in the intake/distribution layer resulting in fluid accumulation in the intake/distribution layer, and then allows fluid transfer to the retention layer when high pressures or high saturation levels occur. It is believed by the inventors that fluid does not preferentially move into the apertures under continuous flow conditions. This controlled transfer mechanism results in an elongated stain pattern in the retention layer and prevents over-saturation in the insult area and provides a visual signal for the wearer indicating product life remaining.

Under gush flow conditions, the apertures in the transfer delay layer allow fluid to immediately pass through to the underlying retention layer.

Figure 2:
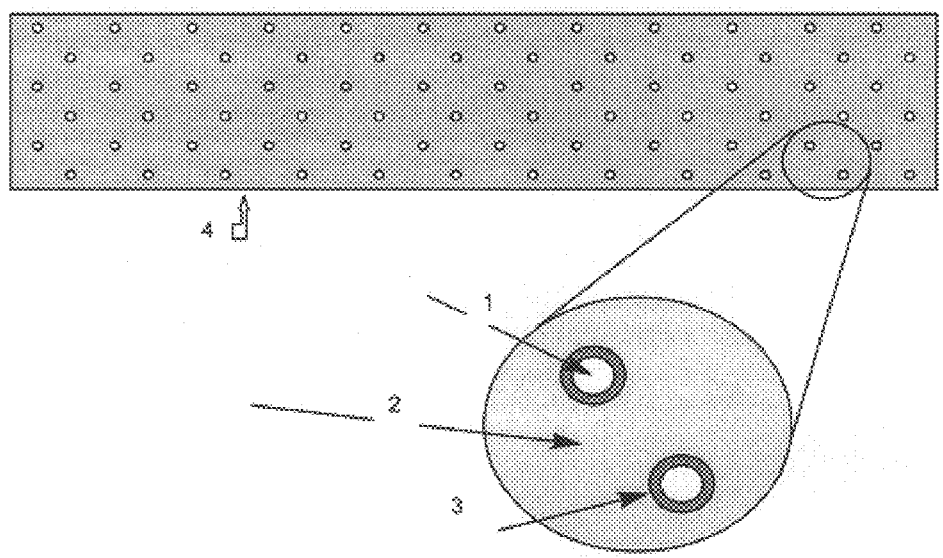
FIG. 2 illustrates the tri-modal pore structure of the co-apertured material.

FIG. 2 illustrates the tri-modal pore structure of the co-apertured material. In FIG. 2, three classes of pores are illustrated. Large pores 1 are located at the point where the fabric was apertured. Smaller pores 2 exist in the original airlaid fabric 4. Yet another class of pores 3 may be found in the area surrounding the point where the fabric was apertured due to densification of the fabric and fiber relocation during the aperturing process.

Figure 3:
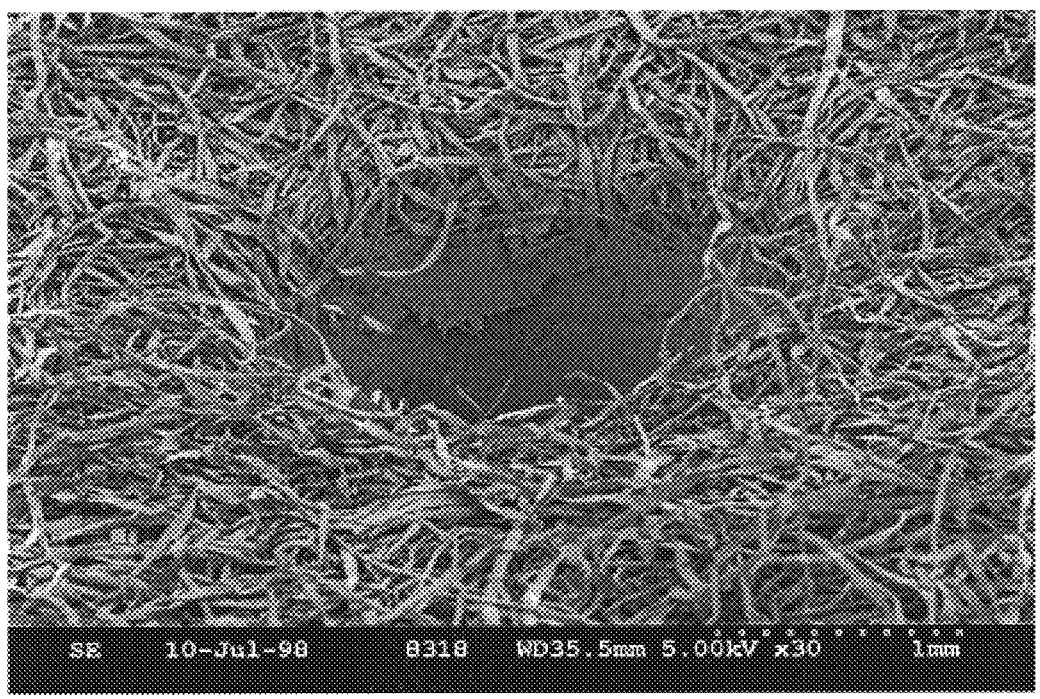
FIGS. 3, 4, and 5 display SEM images of the apertures.
Figure 4:
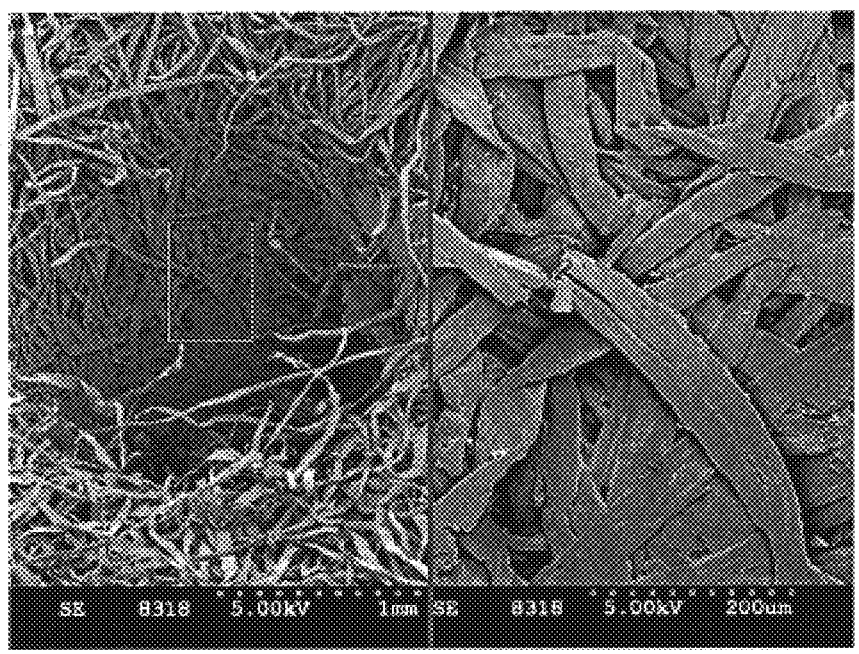
Figure 5:
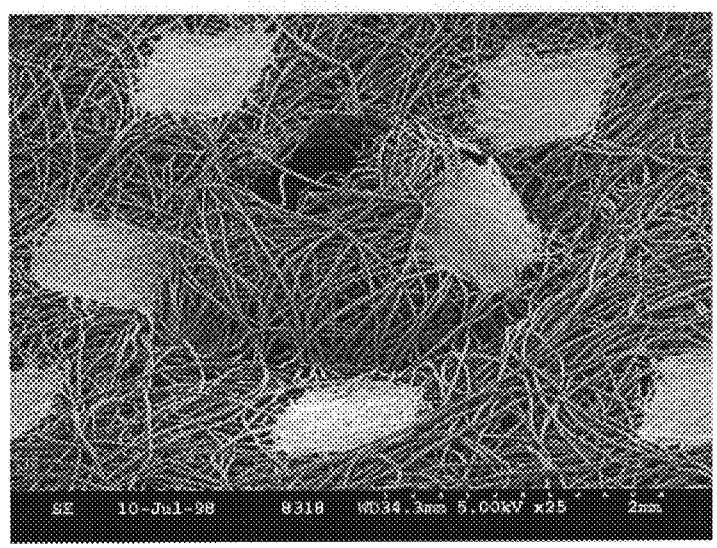

FIGS. 3, 4, and 5 display SEM images of the apertures. FIG. 3 displays an aperture on the airlaid side of the composite at a magnification of one inch (2.54 cm) equals 1 mm. FIG. 4 displays a close-up of an aperture on the airlaid side of the composite at a magnification of one inch equals 200 microns and FIG. 5 displays an aperture from the spunbond side of the composite at a magnification of one inch equals 2 mm.

Figure 6:
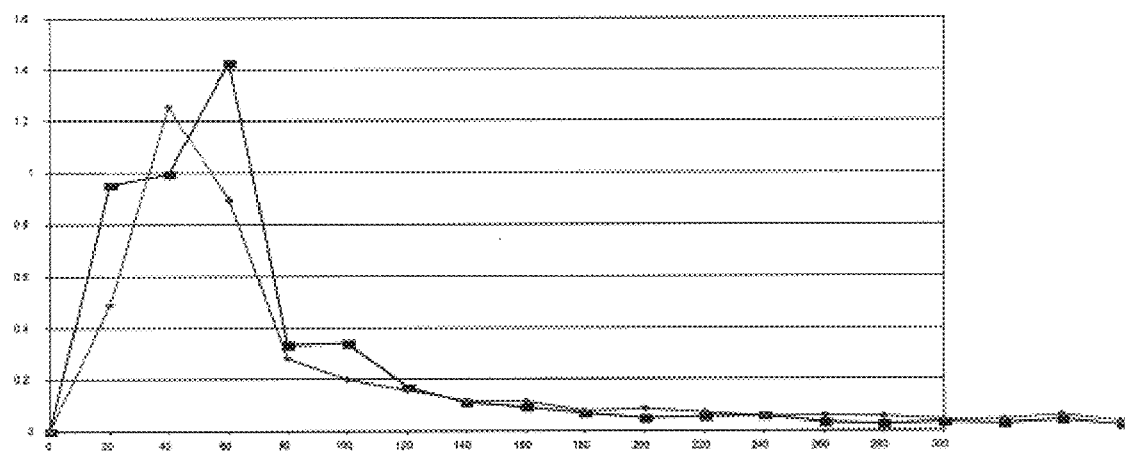
FIG. 6 compares the pore size distribution of an apertured airlaid material to a un-apertured airlaid material.

FIG. 6 compares the pore size distribution of an apertured airlaid material to a un-apertured airlaid material. In FIG. 6 the un-apertured airlaid material is signified by the large dark squares and the apertured (at a pin density of about 2.5 pins/cm$^2$) airlaid material by the lighter colored diamonds. The pore volume (cc/g) is on the Y-axis and the pore radius (microns) on the X-axis. This graph indicates that there is a slight shift toward smaller pores with the apertured material. This is due to a slight densification of the material around the apertures. The large pores which are created by the apertures are not represented in the graph due to their large size. They do, however, provide additional void volume for the material.

Figure 7:
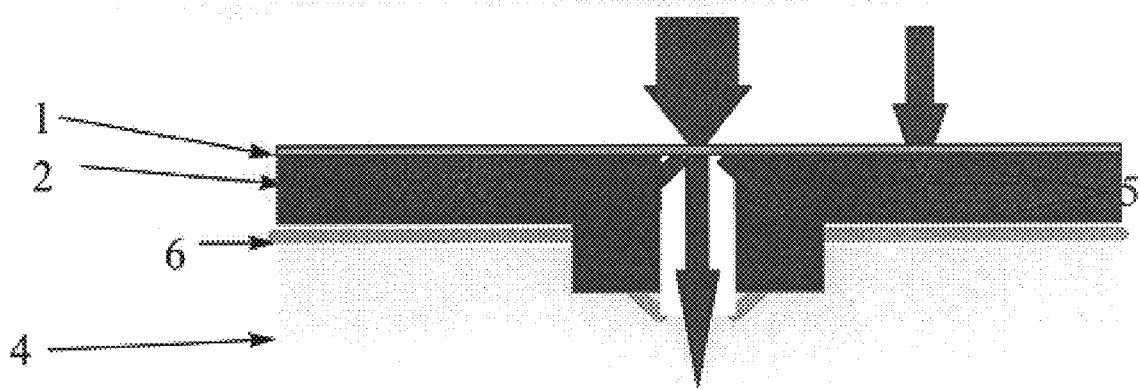
FIG. 7 illustrates the detail of a single aperture and the flow through the material.

FIG. 7 illustrates the detail of a single aperture in relation to the functionality of the absorbent composite. In FIG. 7 an insult (noted by arrows) is delivered to a cover 1. The insult flows through the cover 1 to the co-apertured laminate of the invention where it passes though the intake/distribution layer 2 either at the aperture 3 or through the layer 2 itself. The insult may also be distributed laterally along its length to other areas 5 within the intake/distribution layer 2. Much of the insult eventually passes through the intake/distribution layer 2 and transfer delay layer 6 to the absorbent retention core 4.

The functionality of the co-apertured system can be broken down into five areas: cover desorption, increased surface area, aperture void volume, access to fluff, and wicking capability. Each of these functionality benefits is discussed individually below.

1. Cover Desorption

The un-apertured areas of the intake/distribution layer material maintain a high degree of capillarity after insult and are well suited for desorbing the liner. The small pores of the preferred airlaid material provide the capillarity necessary to desorb the large pores of the cover, thereby removing a majority of fluid from the surface of the product. Improved cover desorption results in low smearing and cover staining levels.

2. Increased Surface Area

The apertured areas of the intake/distribution layer material provide increased surface area for the absorption of fluid. During gush insults, fluid that contacts an aperture can be absorbed in the x, y, and z directions through the wall of the aperture, rather than strictly in the z-direction through the top surface. Therefore, the increased surface area provided by the walls of the apertures enhances the intake characteristics of the airlaid absorbent layer. Additionally, the apertures increase the overall permeability of the intake/distribution layer.

3. Aperture Void Volume

The open areas and void volume created by the apertures allow fluid to be accumulated internally in the product before absorption into the intake/distribution layer material itself. This prevents pooling on the pad surface and facilitates intake when localized saturation of the intake/distribution layer prohibits immediate fluid intake.

4. Access to retention layer

The apertures in the intake/distribution layer material provide a direct fluid pathway to the fluff in the apertured areas. Under gush flow conditions, fluid passes directly through the aperture and into the retention layer. By providing immediate access to retention capacity under these conditions, the void volume of the intake/distribution layer is maintained and intake times for multiple insults are reduced.

5. Wicking Capability

When the intake/distribution layer material is the preferred airlaid fabric, its stability and high degree of wet integrity do not allow the pores to collapse to an appreciable degree when the product is insulted. The stable pore structure allows capillary wicking to laterally transport the fluid out of the insult area and into other regions of the product. The un-apertured areas of the airlaid material maintain this functionality and capillary wicking prevents high saturation from occurring in the insult area. Capillary wicking in combination with the stability of the material allows void volume to be regenerated after an insult so that additional insults can be accepted.

Figure 12:
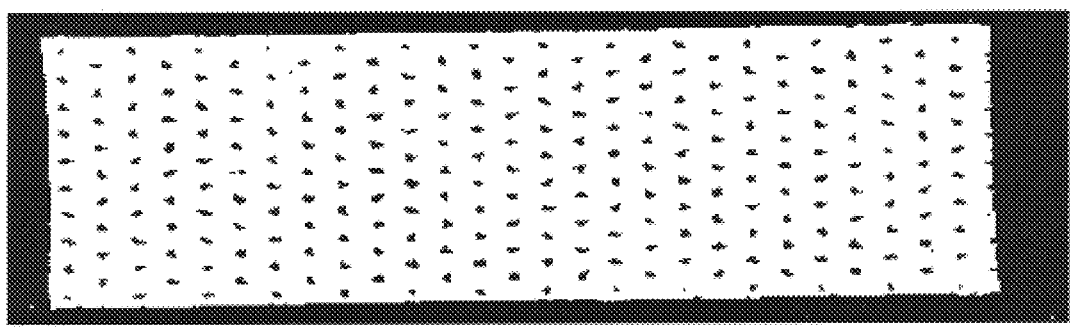
FIG. 12 shows a pin aperturing pattern at 7.4 pins/cm² using 2.06 mm diameter pins.

Experiments were undertaken to examine preferred forms of the invention. Three different basis weights of airlaid fabrics were evaluated: 100, 175, and 250 gsm. Comparisons were made between the three apertured airlaid fabric samples and an un-apertured control sample. The aperturing pattern in FIG. 12 was used initially and had 48 pins/inch$^2$ (7.4 pins/cm$^2$) using 0.081" (2.06 mm) diameter pins.

These materials were tested over a fluff absorbent core using the flat system fluid distribution test. Key measurements included stain size, whether the saturation profile was even or skewed, and the amount of fluid retention and transfer in the airlaid layer. These results are summarized in Table 3.

TABLE 3

Flat System Fluid distribution test - Co-apertured Material Matrix

|  | Apertured* 100 gsm, 0.06 g/cc, 80/20 | Apertured* 175 gsm, 0.08 g/cc, 88/12 | Apertured* 250 gsm, 0.14 g/cc, 90/10 | Control 250 gsm, 0.14 g/cc, 90/10 |
|---|---|---|---|---|
| Stain Size | 12.7 cm | 10.2 cm | 10.2 cm | 15.2 cm |
| Saturation | Even Profile | Even Profile | Even Profile | Even Profile |
| Retention | 3.5 g | 3.8 g | 3.0 g | 4.5 g |
| Transfer | 2.5 g | 2.3 g | 3.0 g | 1.5 g |

*The densities reflected above are pre-apertured densities, the densities of the apertured materials are higher.

This testing showed a decrease in stain length as well as fluid retention in the apertured samples, compared to the control, indicating that aperturing the airlaid fabric increases the density of the airlaid fabric dramatically because the pin density of the initial aperturing pattern (FIG. 12) was so high. This is most noticeable on high basis weight, high original density samples. As the density increases, the pore size and void volume of the fibrous regions of the airlaid materials decrease.

Figure 13:
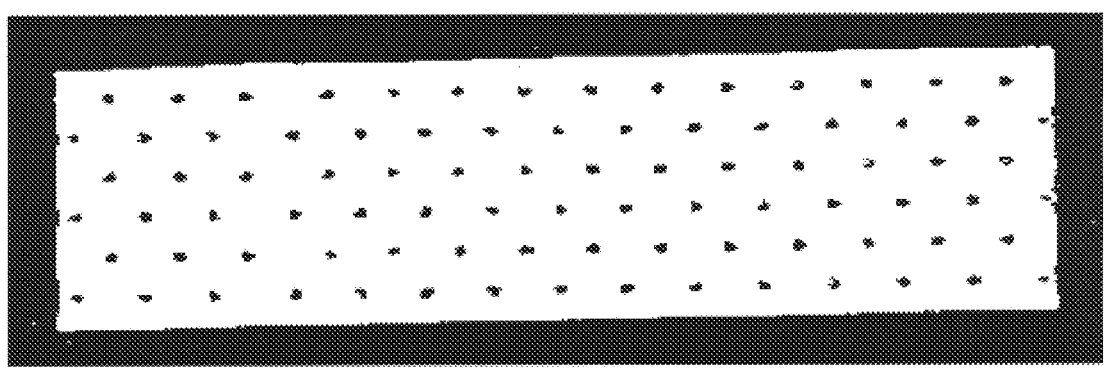
FIG. 13 shows a pin aperturing pattern at 2.5 pins/cm² with the same pin diameter as FIG. 12.

As a result of this sample testing, it was determined that aperturing had the potential to impact product performance. Further testing was performed at a pin density of 16 pins/inch$^2$ (2.5 pins/cm$^2$) (shown in FIG. 13) to minimize increases in post-aperturing material density. The pin diameter remained at 0.081". The range of fabric density studied was narrowed to 175 to 200 gsm and the airlaid fabric was co-apertured to a spunbond fabric transfer delay layer to maintain the intake/distribution functionality.

Tables 4 and 5 display the additional material matrices that were evaluated. The transfer delay layers were spunbond polypropylene fabrics except where film is indicated. The spunbond transfer delay layers had a density and basis weight as indicated. The spunbond fabrics were not treated with surfactants so remained naturally non-wettable. The film was a 1 mil thick polyethylene film.

TABLE 4

Co-apertured Airlaid Material/Transfer Delay Layer

| Basis Weight | Density | Transfer Delay Layer |
|---|---|---|
| 175 gsm | 0.08 g/cc | 27 gsm |
| 175 gsm | 0.08 g/cc | 33.9 gsm |
| 175 gsm | 0.10 g/cc | 27 gsm |
| 175 gsm | 0.10 g/cc | 33.9 gsm |

TABLE 5

Co-apertured Airlaid Material/Transfer Delay Layer

| Basis Weight | Density | Transfer Delay Layer |
|---|---|---|
| 175 gsm | 0.12 g/cc | 27 gsm |
| 175 gsm | 0.14 g/cc | 33.9 gsm |
| 200 gsm | 0.12 g/cc | 27 gsm |
| 200 gsm | 0.12 g/cc | 33.9 gsm |
| 200 gsm | 0.12 g/cc | Film |
| 200 gsm | 0.14 g/cc | 27 gsm |
| 200 gsm | 0.14 g/cc | 33.9 gsm |
| 200 gsm | 1.14 g/cc | Film |

The materials described in Tables 4 and 5 represent materials which were believed to have better performance characteristics potential due to lower aperturing pin density and lower basis weight and/or starting densities. These materials were tested for capacity, horizontal wicking capability, saturation capacity, fluid partitioning characteristics, and triple intake gush capability. Each of these areas is discussed individually below. As a result of this testing, its believed that the pin density should be between about 10 and 40 pins/inch$^2$ (1.6 and 6.2 pins/cm$^2$) for good performance.

Capacity

Figure 14:
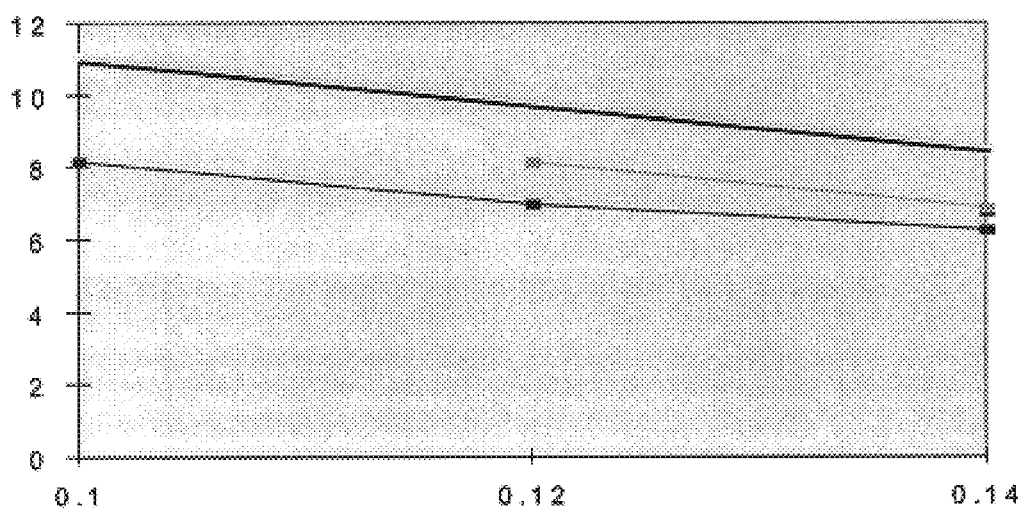
FIG. 14 is a graph the measured capacity for airlaid fabrics with and without apertures where capacity is on the Y-axis and fabric density (cc/g) on the X-axis.

FIG. 14 shows the measured capacity for airlaid fabrics with and without apertures. In FIG. 14, the top line represents the 175 and 200 gsm, un-apertured airlaid fabrics, the middle line a 200 gsm co-apertured airlaid fabric, and the bottom line a 175 gsm co-apertured fabric. Capacity decreases with increasing density as expected. Capacity is also slightly reduced for the apertured samples. This data reveals that an apertured airlaid fabric at 200 gsm and 0.14 g/cc has an equivalent capacity to an un-apertured 175 gsm, 0.14 g/cc fabric.

Horizontal Capillary Wicking—Infinite Reservoir

Horizontal capillary wicking testing was completed to assess the effect of the aperturing process on horizontal wicking distance. Horizontal wicking distance is important to maintain a visual signal which alerts the wearer that the product is nearing capacity and should be replaced. Without appropriate wicking functionality, the visual signal is not present to the desired degree.

Figure 15:
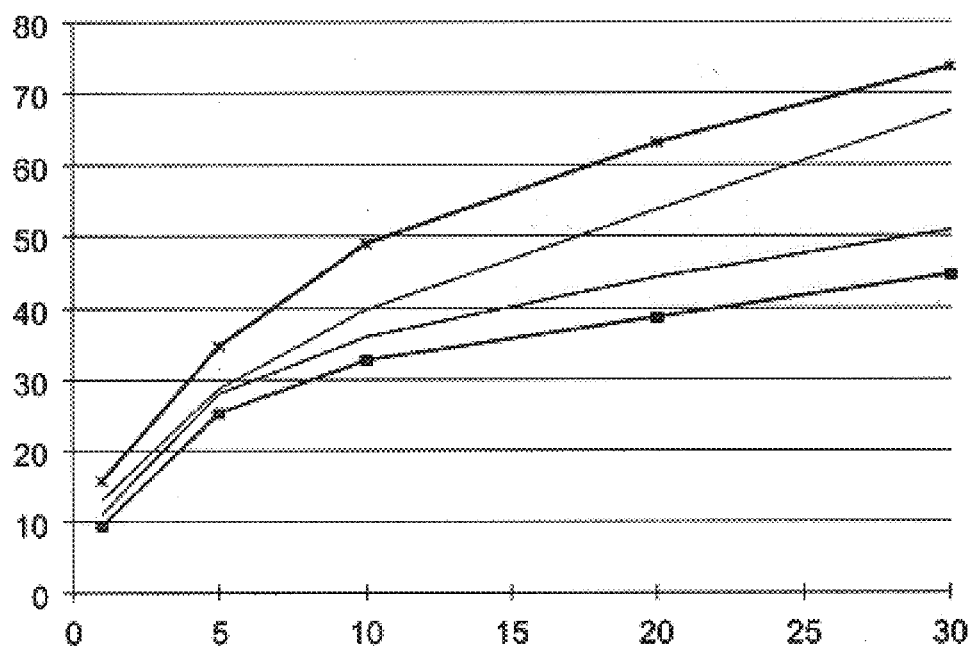
FIG. 15 is a graph of horizontal wicking distance (Y-axis) in mm versus time in minutes for two apertured and two un-apertured airlaid fabrics.

The horizontal capillary wicking results of the 175 gsm low density airlaid samples of Table 4 indicate that aperturing the airlaid material reduces capillary wicking distance. Its believed that the aperturing process creates apertures which disrupt the fluid pathway for wicking and creates density gradients around each aperture. The apertured materials wicked between 17 and 30 mm less than the un-apertured samples, depending on original density. A larger difference existed for materials which had a higher starting density. These results are shown in FIG. 15 where wicking distance in mm is shown on the y-axis and time in minutes on the x-axis. In FIG. 15, the 33.9 gsm un-apertured fabric is the highest line, immediately below it is the line for the 27 gsm un-apertured fabric, followed by the 27 gsm apertured fabric and the 33.9 gsm apertured fabric.

FIG. 15 also indicates that the wicking path disruption associated with aperturing has more impact on horizontal wicking performance than the effect of increased airlaid density. This indicates that the aperturing effect is not a simple densification effect. The horizontal wicking results indicate that there is capillary discontinuity in the apertured samples which results in a significant wicking path disruption.

In an effort to improve wicking distance, higher density airlaid fabric samples were apertured and their capillary wicking performance evaluated. Again the results indicate that the higher density apertured samples do not wick as far as the un-apertured control material. This further showed that capillary disruption is a result of the aperturing process and indicates that capillary wicking distance cannot be controlled by density in the apertured materials.

Wicking Saturation Capacity

To assess the saturation level that results after the capillary wicking process, the saturated materials were sectioned and weighed. The gram per gram saturation level was then calculated to determine how the aperturing process affects the overall gram per gram capacity level of the materials. Note that these saturation levels are based on capillary wicking and not on a dunk and drip protocol.

Figure 16:
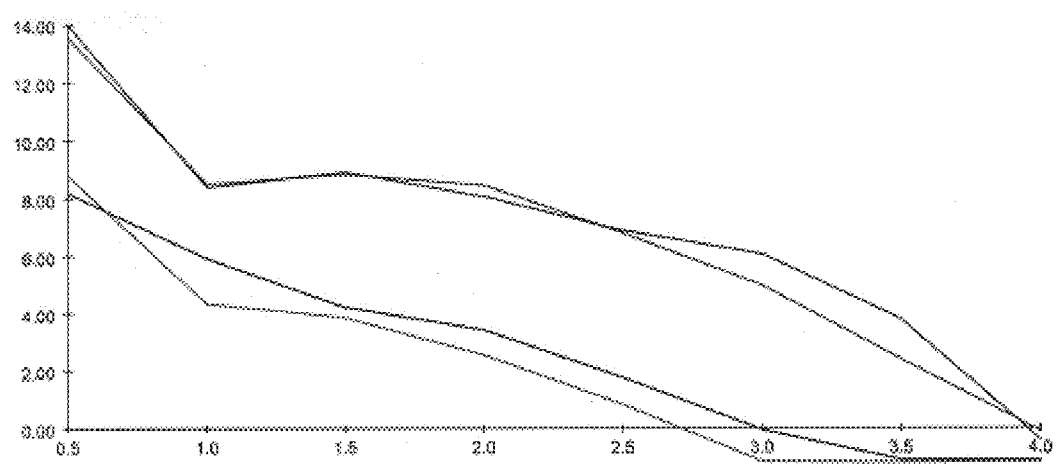
FIG. 16 is a graph of saturation in g/g (Y-axis) versus horizontal wicking distance in inches.

FIG. 16 displays the effect of aperturing on saturation level for the 175 gsm low density airlaid samples of Table 4. The results indicate that not only does horizontal wicking distance decrease as a result of the aperturing process, but wicking saturation capacity decreases also. The apertured samples are much less saturated than the un-apertured samples regardless of starting density though no significant differences were noted between samples that had different starting densities. The effect of aperturing was appeared to be more dominant than the effect of starting density. In FIG. 16, the saturation in g/g is indicated on the y-axis and the wicking distance in inches on the x-axis. The upper most line represents the un-apertured 0.1 g/cc sample, the line below the 0.08 g/cc un-apertured sample, the next line down represents the 0.08 g/cc co-apertured sample and the lowest line the 0.1 g/cc co-apertured sample. All samples are 175 gsm.

The effect of aperturing on the capillary wicking saturation of higher density airlaid materials was also assessed. Again, the apertured samples had lower gram per gram saturation levels than the un-apertured control. It thus appears that basis weight had a minimal effect on horizontal wicking distance or saturation level of the co-apertured samples. The 175 and 200 gsm samples perform similarly and only slight differences were noticed between densities. Overall wicking distance was the same for 0.12 and 0.14 g/cc samples, but the saturation level of the 0.12 g/cc samples was higher, believed to be attributable to the higher void volume of the 0.12 g/cc samples.

Horizontal Capillary Wicking—Demand Absorbency

The objective of aperturing and/or co-aperturing is to increase fluid handling of gush flow while maintaining appropriate fluid intake/distribution and wicking characteristics. Infinite reservoir horizontal wicking tests discussed above have shown that capillary wicking capability and saturation capacity are affected by the aperturing process. Since products experience a variety of pressures and flow conditions in use, wicking potential under demand absorbency was also studied. In the demand absorbency horizontal wicking test, the flat system fluid distribution test method is used and fluid is introduced into the product at a rate of 10 ml/hr.

The results showed that the materials are evenly saturated throughout their length, indicating that wicking is not decreased by aperturing in a demand absorbency wicking setting. Its believed that the stable structure of the airlaid fabric allows the apertured airlaid fabric to be fully utilized even though it does not have the continuous capillary fluid paths that are found in an un-apertured airlaid fabric.

Fluid Partitioning Characteristics Under Demand Absorbency Conditions

Figure 17:
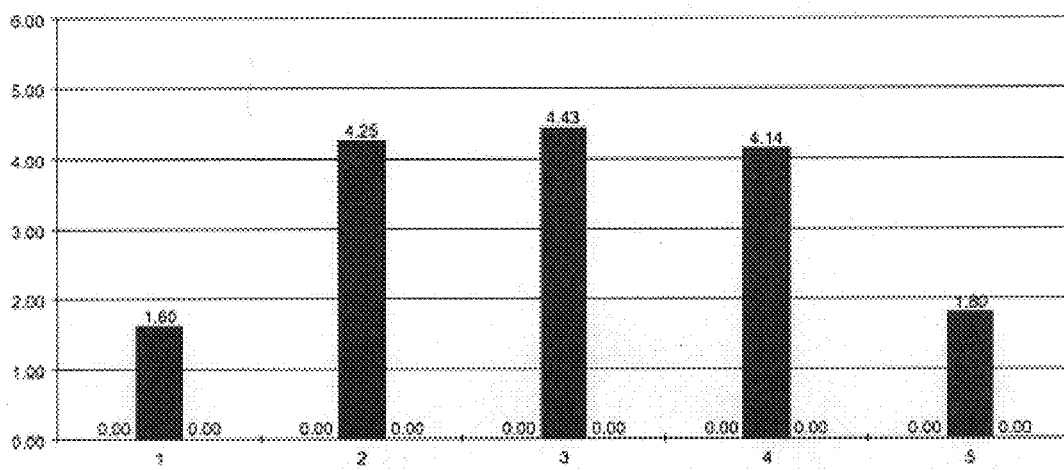
FIG. 17 is a graph of saturation in g/g (Y-axis) versus the pad section as divided according to the flat system fluid distribution test.
Figure 18:
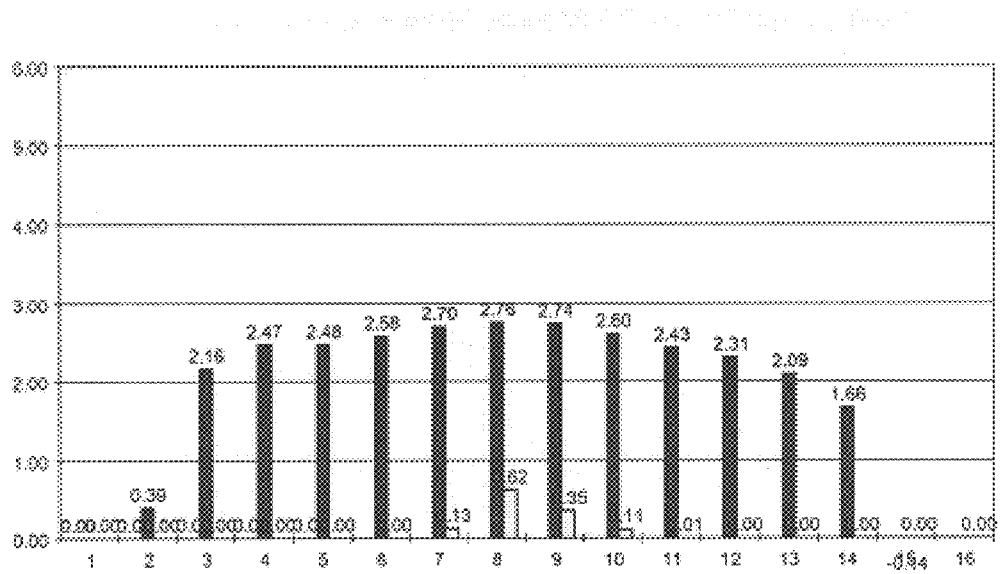
FIG. 18 is a graph of saturation in gig (Y-axis) versus the pad section as divided according to the flat system fluid distribution test.

FIGS. 17 and 18 show the results of a test of the fluid partitioning characteristics of the material. In FIGS. 17 and 18, the cover layer is indicated by a light colored vertical bar, the intake/distribution layer by a dark bar and the fluff perimeter layer by a white bar. In these Figures, the y-axis is the saturation in g/g and the x-axis is the pad section distance from the front edge. The test was carried out at by delivering 5 ml at a rate of 10 mls/hr and under a pressure of 0.25 psi. Fluid partitioning is important in assessing how co-aperturing the airlaid and transfer delay layers changes the fluid transfer characteristics of the product. Ideally, fluid should distribute throughout the entire length of the airlaid layer and transfer though the transfer delay layer simultaneously.

FIG. 17 shows that the control system (un-apertured 175 gsm, 0.14 g/cc airlaid layer using 27 gsm spunbond transfer delay layer) does not allow any fluid transfer to the fluff perimeter layer of the product. FIG. 18 shows that the co-apertured sample (co-apertured 175 gsm, 0.14 g/cc airlaid layer using 0.8 osy spunbond transfer delay layer) does allow transfer to the perimeter fluff layer.

Triple Intake Times

Figure 19:
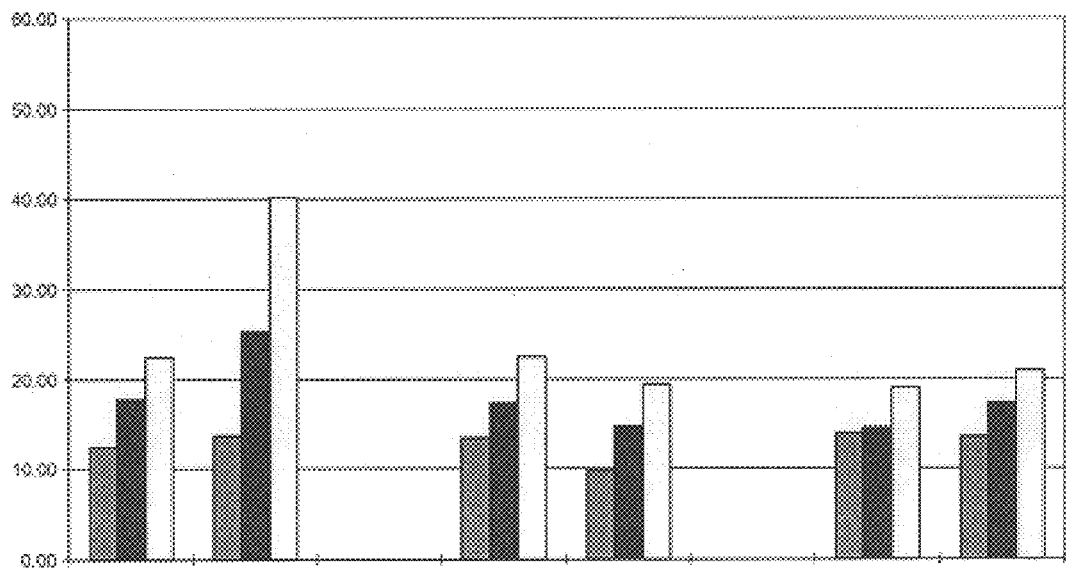
FIGS. 19, 20 and 21 are bar charts of triple gush insult results on various parts of a pad.
Figure 20:
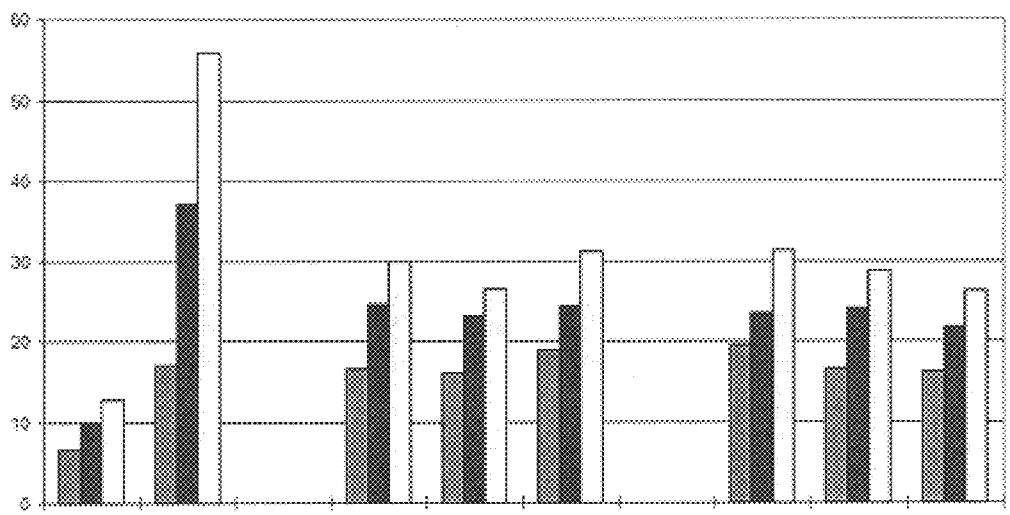
Figure 21:
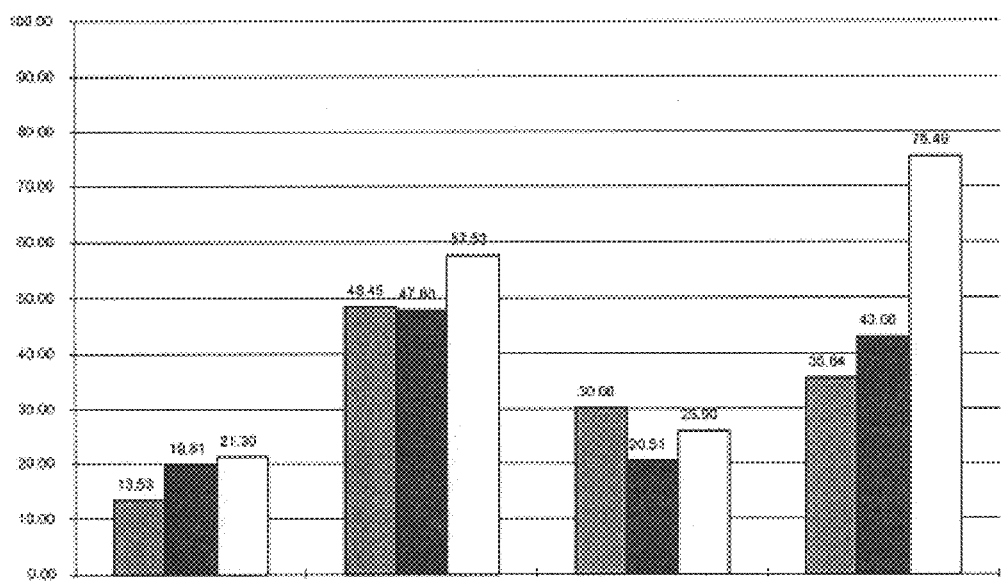

Triple intake testing was completed on a number of airlaid materials to assess the effects of co-aperturing on the intake rates of materials with different starting densities and different transfer delay layers. Testing was done using 3, 2 ml insults, 9 minutes apart. In all of the bar graphs of triple intake testing, the first insult is indicated by a light colored bar, the second in a dark bar and the third in a white bar. The airlaid fabric used in the samples for FIGS. 19 and 20 were made from 90 weight percent NB416 pulp and 10 weight percent Hoescht-Celanese T-255 binder fiber. In FIGS. 19, 20 and 21, the y-axis is the intake time in seconds.

In FIG. 19, the samples, moving from left to right are 175 gsm, 0.10 g/cc apertured airlaid fabric over fluff, 175 gsm, 0.10 g/cc un-apertured airlaid fabric with a 27 gsm spunbond transfer delay layer over fluff, 175 gsm 0.08 g/cc co-apertured airlaid fabric with a 27 gsm spunbond transfer delay layer over fluff, 175 gsm 0.08 g/cc co-apertured airlaid fabric with a 33.9 gsm spunbond transfer delay layer over fluff, 175 gsm 0.10 g/cc co-apertured airlaid fabric with a 27 gsm spunbond transfer delay layer over fluff, 175 gsm 0.10 g/cc co-apertured airlaid fabric with a 33.9 gsm spunbond transfer delay layer over fluff. In FIG. 20, the samples, moving from left to right are 200 gsm, 0.14 g/cc apertured airlaid fabric over fluff, 200 gsm, 0.14 g/cc un-apertured airlaid fabric with a 27 gsm spunbond transfer delay layer over fluff, 200 gsm 0.14 g/cc co-apertured airlaid fabric with a 33.9 gsm spunbond transfer delay layer over fluff, 200 gsm 0.14 g/cc co-apertured airlaid fabric with a 27 gsm spunbond transfer delay layer over fluff, 200 gsm 0.14 g/cc co-apertured airlaid fabric with a 1 mil film delay layer over fluff, 200 gsm 0.12 g/cc co-apertured airlaid fabric with a 1 mil film transfer delay layer over fluff, 200 gsm 0.12 g/cc co-apertured airlaid fabric with a 27 gsm spunbond transfer delay layer over fluff and 200 gsm 0.12 g/cc co-apertured airlaid fabric with a 33.9 gsm spunbond transfer delay layer over fluff.

FIGS. 19 and 20 below show that triple intake times are similar for all of the co-apertured materials tested regardless of which transfer delay layer was used and what density the airlaid fabric was. Triple intake times are higher than a standard airlaid/fluff system and are lower than the same system with a transfer delay but without aperturing. These results indicate that the immediate access to the underlying fluff layer has been greatly improved by co-aperturing.

Triple Intake Testing on a complete gush management absorbent system with a creped cover and co-apertured absorbent system indicate the individual effects of each component.

FIG. 21 displays the triple gush intake results. In FIG. 21, the samples, moving from left to right are creped spunbond fabric cover with 175 gsm 0.12 g/cc co-apertured airlaid fabric with a 27 gsm spunbond transfer delay layer over fluff, un-creped spunbond fabric cover with 175 gsm 0.12 g/cc co-apertured airlaid fabric with a 27 gsm spunbond transfer delay layer over fluff, creped spunbond fabric cover with 175 gsm 0.12 g/cc un-apertured airlaid fabric with a 27 gsm spunbond transfer delay layer over fluff, and uncreped spunbond fabric cover with 175 gsm 0.12 g/cc un-apertured airlaid fabric with a 27 gsm spunbond transfer delay layer over fluff.

The results indicate that combining the creped spunbond cover with a co-apertured intake/distribution/transfer delay layer decreases the intake times and facilitates quicker intake than all of the other samples. It can also be seen from this data that the samples with the creped spunbond cover performed better than the samples with the regular spunbond cover. Co-aperturing made a smaller contribution than did the choice of cover but additional improvements were seen when the creped cover and the co-apertured system were combined. The faster intake times are believed to be a result of the increased fluid transfer to the fluff layer and the void volume that is generated in the intake/distribution layer as a result of this.

The results reveal that the intake/distribution layer should be an airlaid fabric between about 150 and 300 gsm, more particularly between about 175 and 225 gsm, with a density between about 0.05 and 0.18 g/cc, more particularly between about 0.08 and 0.14 g/cc. The transfer delay should be a film, meltblown fabric or spunbond fabric, more particularly a spunbond fabric with a basis weight between about 15 and 50 gsm, still more particularly between about 25 and 35 gsm.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

It should further be noted that any patents, applications or publications referred to herein are incorporated by reference in their entirety.

What is claimed is:

1. A feminine hygiene pad comprising a rapid intake cover adjacent co-apertured intake/distribution and nonwoven transfer delay layers, wherein said transfer delay layer enhances liquid distribution in an X-Y plane of said pad and wherein said co-aperturing produces apertures with walls wherein liquid can be absorbed through the walls of said apertures, which is adjacent an absorbent core retention layer.

2. The pad of claim 1 wherein said cover is made from a process selected from the group consisting of spunbonding, meltblowing, spunlacing, creping, film aperturing, foaming, airlaying, coforming, bonding and carding, and combinations thereof.

3. The pad of claim 2 wherein said cover is made by a spunbond process and has a basis weight between about 10 and 30 gsm and is creped an amount between 20 and 50 percent.

4. The layer of claim 1 wherein said intake/distribution layer horizontally wicks menses a distance of from about 1.2 cm to about 15.25 cm.

5. The pad of claim 1 wherein said transfer delay layer is adjacent said absorbent core.

6. The pad of claim 1 wherein said transfer delay layer is a material selected from the group consisting of spunbond fabric, meltblown fabric, carded fabric and films.

7. The pad of claim 1 wherein said transfer delay layer is a spunbond fabric with a basis weight between about 15 and 50 gsm.

8. The pad of claim 1 wherein said intake/distribution layer is a material selected from the group consisting of airlaid fabric, bonded carded webs, coform materials, hydroentangled pulp fabrics and meltblown fabrics.

9. The pad of claim 8 wherein said intake/distribution layer is an airlaid fabric having a basis weight between about 100 and 300 gsm and a density between about 0.05 and 0.18 g/cc.

10. The pad of claim 1 wherein said intake/distribution and transfer delay layers are co-apertured with pins at a density of between about 1.6 and 6.2 pins/cm$^2$.

11. The pad of claim 1 wherein said intake/distribution and transfer delay layers are co-apertured with pins at a density of about 2.5 pins/cm$^2$.

12. The layer of claim 1 wherein said absorbent core comprises pulp and superabsorbent.

13. The pad of claim 12 wherein said superabsorbent is in a form selected from the group consisting of flakes, particles, spheres, foams and fibers.

14. A feminine hygiene pad comprising a creped spunbond nonwoven fabric outer cover adjacent a pulp airlaid fabric intake/distribution layer having a basis weight between about 175 and 225 gsm and a density between about 0.08 and 0.14 g/cc, co-apertured at a pin density of between about 1.6 and 6.2 pins/cm$^2$ to a polyolefin spunbond nonwoven fabric transfer delay layer having a basis weight between about 25 and 35 gsm, adjacent a retention layer comprising pulp and superabsorbent material.

15. The pad of claim 14 wherein said cover is creped an amount between about 25 and 40 percent and has a basis weight between about 15 and 25 gsm.

16. The pad of claim 14 wherein said airlaid fabric is made from pulp and thermoplastic fibers.

17. The pad of claim 14 wherein said spunbond fabric is made from polypropylene fibers.

18. The pad of claim 14 wherein said creped cover is made from polypropylene fibers.

* * * * *